United States Patent
Kaper et al.

(10) Patent No.: US 8,071,744 B2
(45) Date of Patent: Dec. 6, 2011

(54) TRP/HIS EXCHANGE AND KYNURENIN INDUCED TRP TRANSPORT

(75) Inventors: Thijs Kaper, Palo Alto, CA (US); Michael Platten, Dossenheim (DE); Lawrence Steinman, Stanford, CA (US); Wolf Frommer, Stanford, CA (US)

(73) Assignees: Carnegie Institution of Washington, Washington, DC (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/096,643

(22) Filed: Apr. 28, 2011

(65) Prior Publication Data

US 2011/0223657 A1    Sep. 15, 2011

Related U.S. Application Data

(63) Continuation of application No. 12/040,524, filed on Feb. 29, 2008, now Pat. No. 7,935,494.

(60) Provisional application No. 60/904,166, filed on Mar. 1, 2007.

(51) Int. Cl.
 *C12N 15/62* (2006.01)

(52) U.S. Cl. .................................................. 536/23.4
(58) Field of Classification Search .................. None
See application file for complete search history.

(56) References Cited

U.S. PATENT DOCUMENTS

| | | |
|---|---|---|
| 2004/0157917 A1 | 8/2004 | Gobaille |
| 2005/0064475 A1 | 3/2005 | Endou |
| 2010/0138944 A1 | 6/2010 | Frommer |

*Primary Examiner* — Michael Pak

(74) *Attorney, Agent, or Firm* — Morgan, Lewis & Bockisu LLP

(57) ABSTRACT

The present invention provides methods for detecting changes in tryptophan concentrations in a cell and methods for identifying agents that modulate cellular tryptophan concentrations. In particular, the present invention provides methods for detecting cellular exchange between tryptophan and kynurenine, and methods for identifying agents that modulate this exchange. The present invention also provides methods for treating a disease associated with immunosuppression in a subject in need thereof. In particular, the present invention is directed toward a method of treating a disease associated with immunosuppression comprising contacting the disease with an agent that modulates cellular Trp/kynurenine exchange. Furthermore, the present invention provides methods for identifying an agent that modulates an immunosuppression.

14 Claims, 12 Drawing Sheets

SEQUENCE LISTING

```
<160> NUMBER OF SEQ ID NOS: 7

<210> SEQ ID NO 1
<211> LENGTH: 108
<212> TYPE: PRT
<213> ORGANISM: Artificial
<220> FEATURE:
<223> OTHER INFORMATION: A tryptophan binding protein moiety from E.
      coli

<400> SEQUENCE: 1

Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
                20                  25                  30

Asp Leu His Leu Pro Leu Leu Asn Leu Met Leu Thr Pro Asp Glu Arg
            35                  40                  45

Glu Ala Leu Gly Thr Arg Val Arg Ile Val Glu Glu Leu Leu Arg Gly
        50                  55                  60

Glu Met Ser Gln Arg Glu Leu Lys Asn Glu Leu Gly Ala Gly Ile Ala
65                  70                  75                  80

Thr Ile Thr Arg Gly Ser Asn Ser Leu Lys Ala Ala Pro Val Glu Leu
                85                  90                  95

Arg Gln Trp Leu Glu Glu Val Leu Leu Lys Ser Asp
                100                 105

<210> SEQ ID NO 2
<211> LENGTH: 54
<212> TYPE: DNA
<213> ORGANISM: Artificial
<220> FEATURE:
<223> OTHER INFORMATION: Forward primer

<400> SEQUENCE: 2
ggggacaagt ttgtacaaaa aagcaggctc ggcccaacaa tcaccctatt cagc         54

<210> SEQ ID NO 3
<211> LENGTH: 54
<212> TYPE: DNA
<213> ORGANISM: Artificial
<220> FEATURE:
<223> OTHER INFORMATION: Reverse primer

<400> SEQUENCE: 3
ggggaccact ttgtacaaga aagctgggtt atcgcttttc agcaacacct cttc         54
```

```
<210> SEQ ID NO 4
<211> LENGTH: 37
<212> TYPE: DNA
<213> ORGANISM: Artificial
<220> FEATURE:
<223> OTHER INFORMATION: Forward primer

<400> SEQUENCE: 4
ggtaccggag gcggcgttaa ccacaccaag tctatcg                              37

<210> SEQ ID NO 5
<211> LENGTH: 36
<212> TYPE: DNA
<213> ORGANISM: Artificial
<220> FEATURE:
<223> OTHER INFORMATION: Reverse primer

<400> SEQUENCE: 5
ggtaccggcg cctttacgac gatagtcgcg gaacgg                               36

<210> SEQ ID NO 6
<211> LENGTH: 46
<212> TYPE: DNA
<213> ORGANISM: Artificial
<220> FEATURE:
<223> OTHER INFORMATION: Primer

<400> SEQUENCE: 6
gaaatcggcg tcatccccgg cccgctggaa cagaacaccg gcgcag                    46

<210> SEQ ID NO 7
<211> LENGTH: 46
<212> TYPE: DNA
<213> ORGANISM: Artificial
<220> FEATURE:
<223> OTHER INFORMATION: Primer

<400> SEQUENCE: 7
ctgcgccggt gttctgttcc agcgggccgg ggatgacgcc gatttc                    46
```

TRP/HIS EXCHANGE AND KYNURENIN INDUCED TRP TRANSPORT

CROSS-REFERENCE TO RELATED APPLICATIONS

This application is a continuation of U.S. patent application Ser. No. 12/040,524, filed Feb. 29, 2008 now U.S. Pat. No. 7,935,494, which claims benefit of priority to U.S. Provisional application 60/904,166, filed Mar. 1, 2007, all of which are incorporated herein by reference in their entirety.

STATEMENT OF GOVERNMENT SUPPORT

This work was supported by a grant from the National Institutes of Health (NIH 5R33 DK70272). The government may have certain rights to this invention.

FIELD OF INVENTION

The present invention relates generally to methods for monitoring tryptophan levels in a cell, and more specifically to monitoring the metabolism of tryptophan to kynurenine, and the resulting flux in tryptophan concentration between the intracellular and extracellular spaces. The present invention also relates generally to identifying an agent that modulates immunosuppression by employing the use of a tryptophan fluorescence resonance energy transfer (FRET) nanosensor. Further, the invention provides methods for treating a disease associated with immunosuppression in a subject in need thereof comprising, contacting the subject with or administering to the subject a therapeutically effective amount of at least one agent that modulates the coupled counterexchange of tryptophan for kynurenine or one of its degradation products.

BACKGROUND OF INVENTION

L-Tryptophan is an essential amino acid necessary for protein synthesis in mammalian cells. In addition, tryptophan is the precursor for the neurotransmitter serotonin, the hormone melatonin, and contributes to the synthesis of the coenzymes NAD and NADP. Abnormalities in serotonin production or signaling are related to depression, anxiety and substance abuse (Gingrich et al. (2001) Psychopharmacology (Berl) 155:1-10). Melatonin is necessary for regulation of somatic day-night rhythm (Saper et al. (2005) Nature 437:1257-1263). Mammalian cells cannot synthesize L-tryptophan and depend on transport machineries for its uptake and protein turnover for its production. Identified transporter proteins that are involved in uptake of tryptophan in human cells are $b^0AT1$ (Broer et al. (2005) Biochem. Soc. Trans. 33:233-236), $b^{0,+}AT$ (Feliubadalo et al. (1999) Nat. Genet. 23:52-57), TAT1 (Kim et al. (2002) Genomics 79:95-103), y+-LAT1 and y+-LAT2 (Pfeiffer et al. (1999) EMBO J. 18:49-57; Torrents et al. (1998) J. Biol. Chem. 273:32437-32445), LAT1, LAT2, LAT3 and LAT4 (Babu et al. (2003) J. Biol. Chem. 278: 43838-43845; Bodoy et al. (2005) J. Biol. Chem. 280:12002-12011; Rossier et al. (1999) J. Bio. Chem. 274:34948-34954; Verrey et al. (2003) Eur. J. Physiol. 44:529-533). Of these, $b^{0,+}AT$, LAT1, LAT2, y+-LAT1, and y+-LAT2 are amino acid exchangers; they swap an internal amino acid molecule for an external one.

Tryptophan can be degraded through the kynurenine (or kynurenin) pathway for the biosynthesis of niacin. The rate-limiting step in this pathway is the opening of the indole ring by indoleamine 2,3-dioxygenase (IDO). Since the discovery that inhibition of IDO induced fetal allograft rejection in mice, the immunosuppressive function of tryptophan catabolism has been well established (Munn et al. (1998) Science 281:1191-1193). One proposed mechanism for the observed immunosuppression is the local depletion of tryptophan, which inhibits adaptive T-cell responses by forcing them into growth arrest and inducing apoptosis (Mellor et al. (2003) Adv. Exp. Med. Biol. 527). As such, the immune escape of many cancer cell types correlates with upregulated IDO expression and can in some cases be overcome by IDO inhibition (Muller et al. (2005) Nat. Med. 11:312-319). In addition, products of the kynurenine pathway are immunosuppressive themselves and may provide leads for the treatment of autoimmune disorders such as multiple sclerosis (Platten et al. (2005) Science 310:850-855). The transport machinery for the displacement of kynurenines across the cell membrane is not known.

Traditionally, cellular uptake of molecules has been determined using radiolabeled substrates, and levels have been measured in cell extracts via liquid chromatography or gas chromatography/mass spectrometry. Both methods are neither time-resolved nor specific, and lack high temporal or cellular/subcellular resolution. Tryptophan is also aromatic, and binds to many molecules non-specifically. Given the importance of L-tryptophan for human health, an analytical tool for non-invasive, time-resolved determination of intracellular L-tryptophan levels was deemed highly desirable.

Fluorescent indicator proteins (FLIPs) have been successful tools for real-time monitoring of metabolite levels in living cells. Typically, the nanosensors consist of a ligand-sensing domain, allosterically coupled to a pair of green fluorescent protein variants capable of resonance energy transfer, referred to as Förster Resonance Energy Transfer (FRET) or fluorescence resonance energy transfer. FRET efficiency depends on the distance between and relative orientation of the dipoles of the fluorophores. Ligand-binding induced conformational changes in the sensors result in altered FRET efficiencies, which correlate with the levels of the respective metabolites. Periplasmic binding proteins (PBPs) have been successfully exploited for the construction of FLIPs for imaging of key metabolites such as glucose (Fehr et al. (2003) J. Biol. Chem. 278:19127-19133) maltose (Fehr et al. (2002) Proc. Natl. Acad. Sci. USA 99:9846-9851), ribose (Lager et al. (2003) FEBS Lett. 553:85-89) and glutamate (Okumoto et al. (2005) Proc. Natl. Acad. Sci. USA 102:8740-8745). However, no tryptophan-binding PBPs have been described to date, thus an alternative ligand-sensing scaffold was explored for construction of a tryptophan nanosensor.

In γ-proteobacteria like *Escherichia coli*, transcription of the tryptophan biosynthetic operon is regulated by attenuation (Yanofsky (1981) Nature 289:751-758), and by the inhibitory binding of the tryptophan-activated repressor protein, TrpR, to the trp operator (Joachimiak et al. (1983) Proc. Natl. Acad. Sci. USA 80:668-672). Binding of L-tryptophan to the repressor results in conformational changes that enhance the repressor's affinity for the operator sequence (Zhang et al. (1987) Nature 327:591-597).

SUMMARY OF THE INVENTION

The present invention provides a drug screening method. The present invention utilizes the ligand-induced conformational changes of TrpR for the construction of novel genetically encoded sensors for monitoring of in vivo L-tryptophan levels. This demonstrates the applicability of metabolite FRET nanosensor technology to novel ligand-sensing domains and instigates new methods for the construction of nanosensors for metabolites that are only present inside the cell (and therefore are unlikely to be recognized by evolved PBPs). In addition, the invention described herein provides a novel strategy for the optimization of the FRET signal based on the particular topology and conformation of TrpR. An optimal FRET nanosensor helped characterize the tryptophan transporting machinery in COS-7 cells. Importantly, the FRET nanosensors can observe the coupled counterexchange of intracellular tryptophan for extracellular kynurenine, providing a new metabolic cycle that may contribute to the immune escape of various tumor cells and the favorable role of kynurenines in reducing autoimmunity while protecting the cells that overproduce IDO from kynurenine accumulation.

The present inventors have identified a novel metabolic cycle involving a LAT-type amino acid exchanger that mediates the counterexchange of tryptophan for its kynurenine or its degradation products. Both tryptophan depletion and elevated kynurenine serum levels have an immunosuppressive function. The discovered LAT exchange activity means that indoleamine-2,3-dioxygenase-catalyzed tryptophan degradation and LAT-mediated tryptophan/kynurenine exchange are the components of a cycle that combines serum tryptophan sequestration with kynurenine accumulation. Consequently, this mechanism may contribute to immunosuppression involved in autoimmunity tumor immune escape. Importantly, the cycle creates a two-pronged mechanism to induce growth arrest and apoptosis, while at the same time protecting kynurenine producing cells from increasing kynurenine levels.

The present invention provides methods for monitoring the steady-state, the uptake, and the counter-exchange of tryptophan. In some embodiments, the concentration of tryptophan is detected or monitored. In other embodiments, the changes in the concentration of tryptophan inside the cell are observed. Changes to tryptophan concentrations may result after certain stimuli, such as perfusing a cell with an amino acid (e.g. L-histidine, kynurenine, L-tryptophan), treatment of a cell with an agent, or increasing or decreasing the activity of IDO. Moreover, the extracellular concentration of tryptophan may be detected or monitored. The levels of kynurenine may also be detected or monitored. Detection may involve quantitating the levels of tryptophan, kynurenine, other amino acids, agents, or enzymes.

The present invention provides for the detection of tryptophan through the use of Förster Resonance Energy Transfer (FRET). The present invention provides a FRET fusion protein comprised of an acceptor fluorophore moiety, a donor moiety, and a tryptophan binding domain. In some embodiments there are at least two tryptophan binding domains. In other embodiments, other polypeptide domains are fused to the FRET fusion protein, such as purification tags, other binding domains and localization sequences. Methods known in the art for detecting tryptophan and its metabolites, such as kynurenine, also may be utilized. By way of example, tryptophan and kynurenine may be detected by chromatography, such as high performance chromatography. Tryptophan and kynurenine may further be detected and monitored through the use of radio-labeling, spectrophotometry, fluorescence, chemoluminescence, antibody binding, electro-chemical sensors, and nuclear magnetic resonance spectrophotometry.

The present invention provides a method for detecting tryptophan in a cell comprising: providing the cell with an isolated nucleic acid, wherein the nucleic acid encodes a donor fluorophore moiety, an acceptor moiety, and a tryptophan binding moiety; and, detecting a change in Förster Resonance Energy Transfer (FRET) between the donor moiety and the acceptor moiety, thereby detecting tryptophan in the cell. The method may further comprise detecting extracellular level of tryptophan. The cell may be perfused extracellularly with an amino acid.

The tryptophan level in the cell may increase or decrease through exchange with extracellular amino acids via an amino acid transporter. Tryptophan is transported in and out of the cell by a L-amino acid transporter, such as LAT-1 or LAT-2.

In one embodiment, the present invention discloses a method of measuring or quantitating tryptophan levels in a cell comprising providing the cell with an isolated nucleic acid, wherein the nucleic acid encodes a donor fluorophore moiety, an acceptor moiety, and a tryptophan binding moiety; measuring the change in FRET between the donor moiety and the acceptor moiety, thereby measuring tryptophan in the cell. The tryptophan level in the cells may be measured using a calibration curve. The calibration curve may be obtained by titration.

In another embodiment, the present invention provides a method of detecting tryptophan/kynurenine exchange comprising: providing a cell expressing a tryptophan/kynurenine transporter; providing the cell with an isolated nucleic acid, wherein the nucleic acid encodes a donor fluorophore moiety, an acceptor moiety, and a tryptophan binding moiety; detecting a change in FRET between the donor moiety and the acceptor moiety, thereby detecting tryptophan/kynurenine exchange. The cell may also express indoleamine 2,3-dioxygenase (IDO). A nucleic acid encoding IDO may be introduced into the cell to enable it to express IDO. The method may further comprise detecting the level of kynurenine.

The present invention also discloses a method of identifying an agent that modulates tryptophan concentration in a cell comprising: providing the cell with an isolated nucleic acid, wherein the nucleic acid encodes a donor fluorophore moiety, an acceptor moiety, and a tryptophan binding moiety; exposing the cell to a test agent; detecting a change in FRET between the donor moiety and the acceptor moiety, thereby identifying an agent that modulates tryptophan concentration. In one embodiment, the agent may modulate tryptophan concentration by directly affecting an amino acid transporter responsible for tryptophan influx and efflux with the extracellular space. In another embodiment, the agent may modulate tryptophan concentration by directly affecting an enzyme responsible for tryptophan metabolism. The enzyme may be IDO.

Moreover, the present invention provides a method of identifying an agent that modulates tryptophan/kynurenine exchange comprising: providing a cell expressing a tryptophan/kynurenine transporter; providing the cell with an isolated nucleic acid, wherein the nucleic acid encodes a donor fluorophore moiety, an acceptor moiety, and a tryptophan binding moiety; exposing the cell to a test agent; detecting a change in FRET between the donor moiety and the acceptor moiety, thereby identifying an agent that modulates tryptophan/kynurenine exchange. The tryptophan/kynurenine transporter may be a L-amino acid transporter, such as LAT-1 or LAT-2.

Additionally, the present invention provides a method of identifying an agent that modulates immunosuppression comprising: providing a cell that is associated with immunosuppression that expresses a tryptophan/kynurenine transporter; providing the cell with an isolated nucleic acid, wherein the nucleic acid encodes a donor fluorophore moiety, an acceptor moiety, and a tryptophan binding moiety; exposing the cell to a test agent; detecting a change in FRET between the donor moiety and the acceptor moiety, thereby identifying if the agent modulates immunosuppression. As an example, the cell may be a T cell. Also, the IDO may be expressed in the cell associated with immunosuppression.

The present invention also provides methods for identifying an agent that modulates a disease involving immunosuppression, comprising: applying the agent to a biological sample obtained from a site of the disease; introducing tryptophan FRET nanosensor into the sample; and subsequently observing changes in tryptophan using a tryptophan FRET nanosensor, wherein a change in the tryptophan concentration is indicative of an agent that modulates immunosuppression. The method may further comprise identifying immunosuppression by any method known in the art such as growth arrest or apoptosis. In one embodiment, the disease is cancer. In another embodiment, the disease is selected from the group consisting of autoimmune disease and inflammatory disease.

The methods described above may also involve:
(a) measuring tryptophan concentration in a cell using a tryptophan fluorescence resonance energy transfer (FRET) nanosensor;
(b) applying the agent to the cell; and
(c) subsequently measuring tryptophan concentration in the cell in (a) using a tryptophan FRET nanosensor;
wherein a change in the tryptophan concentration in (c) compared to the tryptophan concentration in (a) is indicative of an agent that modulates immunosuppression.

The methods described above may be performed with a sample of cells. The cell or cells may be in a biological sample. The biological sample may be biological fluids or tissues from a subject. The subject may be diagnosed with or suffering from a disease and is in need of treatment. The disease may be associated with immunosuppression.

The agents identified by the method of the present invention may affect an enzyme that metabolizes tryptophan. The enzyme may be IDO. An example of an agent may be 2-aminobicyclo-(2,2,1)-heptane-2 carboxylic acid (BCH) or analogs or derivatives thereof.

The agents identified by the method of the present invention may increase or decrease the concentration of tryptophan in the cell. The agent may increase the exchange of tryptophan for amino acids. The agent may increase the rate of exchange of tryptophan for kynurenine. The agent may modulate an amino acid counter-exchanger such as a L-amino acid transporter selected from the group consisting of LAT-1 or LAT-2.

The agents identified by the method of the present invention may modulate the exchange of tryptophan for kynurenine through a L-amino acid transporter. In one embodiment, the agent inhibits the counterexchange of tryptophan for kynurenine or its degradation products. The agent may be a system L inhibitor. The system L inhibitor may be 2-aminobicyclo-(2,2,1)-heptane-2 carboxylic acid (BCH). In another embodiment, the agent may promote the counterexchange of tryptophan for kynurenine or its degradation products.

The agent identified by the method of the present invention may increase the expression of indoleamine 2,3-dioxygenase (IDO). The agent may be a nucleic acid molecule encoding functional indoleamine 2,3-dioxygenase (IDO) or a fragment thereof.

The agent may be a cytokine. The cytokine may be interferon-γ (IFN-γ). IFN-γ may induce the enzymatic degradation of tryptophan by IDO. IFN-γ may further enhance the exchange of tryptophan for kynurenine. IFN-γ may further be administered to a cell with another agent. In some embodiments, the other agent may enhance, either additionally or synergistically, the effects of IFN-γ. In other embodiments, the other agent may inhibit or block the effects of IFN-γ.

In some embodiments, the agent is selected from the group consisting of a RNAi, an antisense RNA, or a chemical (small molecule).

The agent identified by the method may affect the activity of IDO. In some embodiments the agent may increase the activity of IDO. In other embodiments, the agent may inhibit or block the activity of IDO.

The present invention also provides methods for determining if a subject is prone to immunosuppression. In some embodiments, the activity of IDO affects kynurenine production, thereby affecting T cell activity. In certain embodiments, IDO activity is increased. In other embodiments, IDO activity is suppressed, such as with 1-methyl-tryptophan. IDO may be expressed endogenously, in cells such as cancer cells, dendritic cells, maternal cells such as placental cells, fetal cells such as syncytiotrophoblasts, and cells involved in immune privileged areas, such as the testes, thymus, eyes, uterus, and brain. IDO expression may be further introduced into a cell, such as through transfection. Expression of IDO may be further regulated through the use of an inducible promoter, such as through the use of nuclear receptor heterodimer binding domains.

The present invention also provides methods to determine whether a T cell is prone to growth arrest or apoptosis. In some embodiments, detecting the intracellular concentration of tryptophan indicates the vulnerability of a T cell to growth arrest or apoptosis. In other embodiments, modulations in tryptophan levels may affect a T cell's vulnerability to growth arrest or apoptosis. In certain embodiments, depletion of tryptophan may lead a T cell to growth arrest or apoptosis. In other embodiments, increasing tryptophan levels may prevent a T cell's growth arrest or apoptosis.

The present invention provides a method for treating a subject in need thereof. The subject may be suffering from or diagnosed with a disease involving immunosuppression. The method of the present invention comprises: contacting the subject with or administering to the subject a therapeutically effective amount of at least one agent that modulates coupled counterexchange of tryptophan for kynurenine or a catabolite of kynurenine across a cell membrane. In one embodiment, the subject is an animal. In another embodiment, the animal is a mammal, such as a human.

The present invention may also be used to diagnose immunosuppression in a subject comprising obtaining a biological sample from the subject; determining tryptophan concentration of the sample using a biosensor comprising a donor fluorophore moiety, an acceptor moiety, and a tryptophan binding moiety for detecting a change in FRET between the donor moiety and acceptor moiety; and comparing the tryptophan concentration to that of a control sample to determine whether the subject is suffering from immunosuppression. A depletion of tryptophan as compared to a control sample from a healthy subject indicates that the subject is suffering from immunosuppression.

The present invention provides a method of protecting against autoimmunity comprising: expressing LAT-1 and IDO in a cell to regulate tryptophan/kynurenine exchange, thereby suppressing T cell activity and protecting against autoimmunity. The kynurenine levels may be increased. The cells may be in a fetus, in a graft or transplant, or cells susceptible to attack from an autoimmune disease.

BRIEF DESCRIPTION OF THE DRAWINGS

The foregoing summary, as well as the following detailed description of the invention, will be better understood when read in conjunction with the appended figures. For the purpose of illustrating the invention, shown in the figures are embodiments which are presently preferred. It should be understood, however, that the invention is not limited to the precise arrangements, examples and instrumentalities shown.

FIG. 1A shows TrpR dimer in complex with L-tryptophan bound to the tip operator (PDB: 1TRO (Otwinowski et al. (1988) Nature 335:321-329). FIG. 1B shows the FLIPW variants. FIG. 1C shows normalized FRET ratio change of FLIPW-CTY in presence of L-tryptophan (filled squares), D-tryptophan (grey circles), 5-hydroxy-L-tryptophan (grey squares) and 5-methyl-L-tryptophan (grey triangles). Ratio is defined as fluorescence intensity quotient of emission at 528 nm/485 nm. FIG. 1D shows normalized FRET ratio change of FLIPW-CTY (filled squares), FLIPW-TCTY (grey circles), FLIPW-CTYT (grey triangles), and FLIPW-CTTY (grey squares) in the presence of L-tryptophan.

FIG. 2A shows the dimer of two FLIPW-CTY chains resulting in a TrpR dimer that can bind tryptophan. FIG. 2B shows the FLIPW-CTYT monomer.

FIG. 3A show FRET ratio change of cell cultures in presence of Tyrode's buffer (squares) and 100 µM L-tryptophan in Tyrode's buffer (circles). Data correspond to means±S.E. (n=12). FIG. 3B shows the velocity of intracellular FLIPW-CTYT response versus external tryptophan concentration fitted with the Michaelis-Menten equation. Cells were incubated with 0.05, 0.1, 0.25, 0.5, 1, 5, 10 and, 25 µM L-tryptophan. Data correspond to means±S.E. (n=6). Ratios are defined as fluorescence intensity quotient of emission at 528 nm/485 nm.

FIG. 4A shows the perfusion of COS-7 cells with various concentrations L-tryptophan (L-Trp) and 100 µM L-histidine (L-His) in Tyrode's buffer. According to the FRET theory, an increase in VENUS signal is accompanied by a decrease in ECFP signal. Ratio defined as fluorescence intensity quotient obtained with emission filters 535/40 nm over 480/30 nm. FIG. 4B shows the velocity of intracellular FLIPW-CTYT response versus external tryptophan concentrations used in panel A fitted with the Michaelis-Menten equation. Bars indicate standard deviation. FIG. 4C shows the effect of $Na^+$-ions and inhibitors on the uptake rate of 100 µM L-tryptophan. Bars indicate standard deviation.

FIG. 5A show the molecular structures of L-tryptophan, (3-hydroxy)-L-kynurenine, and 3-hydroxy-anthranilic acid. FIG. 5B shows the perfusion of COS-7 cells with 100 µM L-tryptophan (L-Trp), 100 µM L-histidine (L-His), and 200-1000 µM 3-hydroxy-DL-kynurenine (DL-HK) in Tyrode's buffer. According to the FRET theory, an increase in VENUS signal is accompanied by a decrease in ECFP signal. Ratio defined as fluorescence intensity quotient obtained with emission filters 535/40 nm over 480/30 nm.

FIG. 8 shows the structural models of FLIPW-TCTY and FLIPW-CTYT tryptophan sensors. The TrpR are PDB: 1WRP, the eCFP is based on PDB: 1MYW and the VENUS is PDB: 1MYW.

FIG. 9A shows both the accumulation of kynurenines and depletion of tryptophan arrest T-cell growth and induce apoptosis, permitting a cancerous lesion to escape immune surveillance. FIG. 9B shows IDO overproducing cells are protected from the apoptotic effect of kynurenines by the strict counterexchange of tryptophan and its stoichiometric degradation products. Black circle represents LAT transporter.

FIG. 11A shows an untreated KB cell loaded with tryptophan until the sensor is saturated. Perfusion of the cell with histidine returns the response back to baseline levels. Next, the cell is loaded until the sensor is partially saturated and small changes in tryptophan concentration are easily detected. In the untreated cell, the tryptophan level remains constant during continuous perfusion with Tyrode's buffer and only perfusion with histidine will return the response to baseline levels. Final perfusion with tryptophan and histidine is used to redetermine the maximal response of the sensor. FIG. 11B shows a KB cell treated with 500 U/ml IFNγ loaded with tryptophan to determine the maximal sensor response, and then unloaded with histidine. This time when the cell is loaded until the sensor is partially saturated, the levels drop immediately upon perfusion of the cells with Tyrode's buffer. Within minutes the baseline level is achieved. A final perfusion with tryptophan and histidine illustrates again the maximal response of the sensor.

DETAILED DESCRIPTION OF THE INVENTION

Figure 1A:
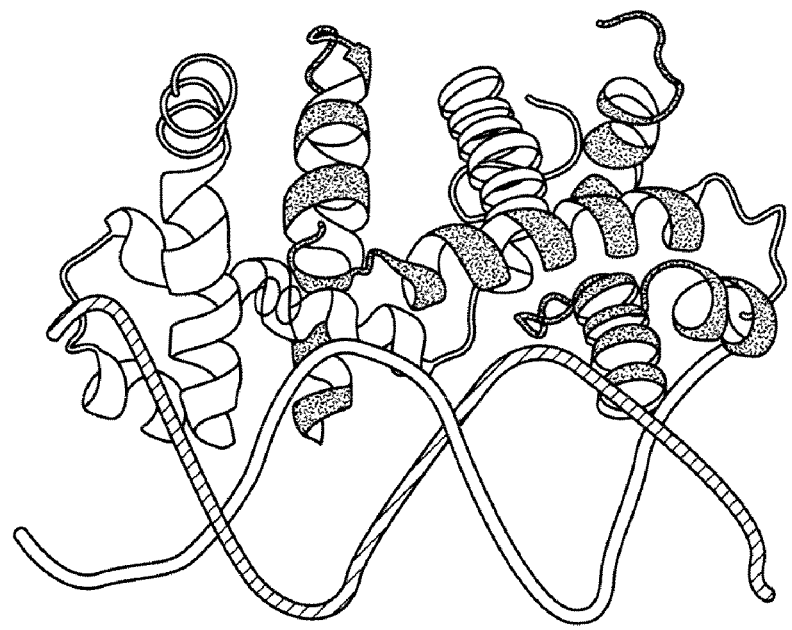
FIGS. 1A-D show the tryptophan sensors based on the *E. coli* tryptophan repressor TrpR.

Unless defined otherwise, all technical and scientific terms used herein have the same meaning as commonly understood by one of ordinary skill in the art to which this invention belongs.

The present invention is based in part on the finding that FRET may be used to detect tryptophan levels in a cell and to monitor the metabolism of tryptophan in a cell.

The present invention provides methods for detecting and monitoring, for example in real time, the levels of tryptophan inside a cell. The present invention also provides methods for quantitatively determining the concentration of tryptophan inside a cell. The present invention further provides methods for determining the extracellular levels of tryptophan, whereby the net influx and efflux of tryptophan over a period of time maybe calibrated and assessed. The present invention also provides methods for calibrating increases and decreases in tryptophan levels, either individually in the intracellular or extracellular spaces, or combined overall in the cell's environment.

The present invention further provides methods for detecting and monitoring the exchange for tryptophan with its metabolite, kynurenine, and derivatives thereof, across a cell membrane. The present invention also includes methods for determining the rate of tryptophan metabolism to kynurenine through the enzyme indoleamine 2,3-dioxygenase (IDO). In particular, the present invention provides methods for determining the rate of tryptophan concentration depletion. In other embodiment, the present invention provides methods for determining the rate of kynurenine production.

The present invention herein provides methods for treating a disease associated with immunosuppression in a subject in need thereof. In particular, the present invention is directed toward a method of treating a disease associated with immunosuppression comprising contacting the disease with a therapeutically effective amount of at least one agent that modulates the coupled counterexchange of tryptophan for kynurenine or its degradation products. Furthermore, the present invention provides methods for identifying at least one agent that modulates a disease involving immunosuppression, comprising: applying the agent and subsequently detecting changes in tryptophan concentration, wherein a change in the tryptophan concentration is indicative of an agent that modulates immunosuppression.

As used herein, the term "autoimmune disease", or "autoimmunity", refers to the immune system of a subject reacting and responding to its own cells, tissues and components thereof. By way of example, autoimmune diseases include diabetes mellitus type 1, systemic lupus erythematosus, celiac disease, Crohn's disease, multiple sclerosis, rheumatoid arthritis, Sjögren's syndrome, Hashimoto's thyroiditis, Goodpasture's syndrome, Guillain-Barré syndrome, Kawasaki's disease, myasthenia gravis, opsoclonus myoclonus syndrome, idiopathic thrombocytopenic purpura, primary biliary cirrhosis, Reiter's syndrome, Addison's disease, acute disseminated encephalomyelitis, Ankylosing spondylitis, aplastic anemia, autoimmune hepatitis, oophoritis, gestational pemphigoid, optic neuritis, Ord's thyroiditis, pemphigus, Gaucher's disease, pernicious anemia, Takayasu's arteritis, and Wegener's granulomatosis.

The immune responses contemplated by the present invention may also include rejection of a transplant, a graft, or an implant. Encompassed within the realm of rejection conditions is graft versus host disease (GvHD). Types of transplant may include autografts, allografts, isografts, xenografts, and domino transplants. Transplants may include the placing of at least one cell into a subject, wherein that at least one other cell originates from another subject or from another region of the subject's own body. Grafts may include the transplanting of tissue without blood supply, such as medical grafts. By way of example, skin and bone may be grafted. Implants may include the placing of an object, made of natural or synthetic components or combinations thereof, into a subject's body, wherein the object serves a function in the subject's body. By way of example, joints, limbs, valves, stents, catheters, pacemakers, bones, and organs may be implanted into a subject. Types of rejection may include acute rejection, chronic rejection or vasculopathy, and hyperacute rejection. Rejection may also include responses to microchimerism. Rejection may further apply to regions that are considered to be immune privileged, such as the eyes, brain, testes, and uterus.

The immune responses contemplated by the present invention may further include immune responses generated by and during pregnancy. These may include reactions to an embryo by the mother, such as allogenic fetal rejection and Rh factor incompatibility. These may also include an embryo or fetus's incompatibility with the mother, such as in Erythroblastosis Fetalis. These may further include postpartum autoimmune responses, such as those listed above, and may be caused by conditions such as fetal microchimerism.

As used herein, the term "biological sample" refers to a sample obtained from an organism or from components (e.g., cells) of an organism. The sample may be of any biological tissue or fluid. The sample may be a sample which is derived from a patient. Such samples include, but are not limited to, sputum, blood, blood cells (e.g., white cells), tissue or biopsy samples (e.g., tumor biopsy), urine, peritoneal fluid, and pleural fluid, or cells therefrom. Biological samples may also include sections of tissues such as frozen sections taken for histological purposes.

As used herein, the term "cancer" includes, but is not limited to, solid tumors, such as cancers of the breast, respiratory tract, brain, reproductive organs, nervous system, digestive tract, urinary tract, eye, retina, bone and joints of bones, bladder, rectum, auditory system, circulatory system including heart, liver, skin, kidney, muscle, cervix, uterus, fallopian tube, testes, prostate, pituitary, esophagus, adrenal glands, paraadrenal glands, pancreas, spleen, stomach, lung, mouth, tongue, trachea, large and small intestines, lymphatic system, head and neck, thyroid, parathyroid, and their distant metastases. The term also includes lymphomas, sarcomas, yeoman, and leukemias. Examples of breast cancer include, but are not limited to, invasive ductal carcinoma, invasive lobular carcinoma, ductal carcinoma in situ, and lobular carcinoma in situ.

As used herein, the term "covalently coupled" means that the donor and acceptor moieties may be conjugated to the ligand binding protein moiety via a chemical linkage, for instance to a selected amino acid in said ligand binding protein moiety. Covalently coupled also means that the donor and acceptor moieties may be genetically fused to the ligand binding protein moiety such that the ligand binding protein moiety is expressed as a fusion protein comprising the donor and acceptor moieties.

As used herein, the term "dsRNA" refers to RNAi molecules, or other RNA molecules including a double stranded feature and able to be processed to RNAi in cells, such as hairpin RNA moieties.

As used herein, the term "isolated" refers to molecules separated from other cell/tissue constituents (e.g. DNA or RNA), that are present in the natural source of the macromolecule. The term "isolated" as used herein also refers to a nucleic acid or peptide that is substantially free of cellular material, viral material, and culture medium when produced by recombinant DNA techniques, or chemical precursors or other chemicals when chemically synthesized. Moreover, an "isolated nucleic acid" may include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the term "loss-of-function" refers to a diminishment in the level of expression of a gene when compared to the level in the absence of RNAi constructs.

As used herein, the term "modulate" refers to such agents may increase or decrease tryptophan binding homeostasis (metabolism & uptake) activity, or may affect activities, i.e., cell functions or signaling cascades, that affect tryptophan levels. Agents that increase or decrease tryptophan homeostasis (metabolism & uptake) activity may be targets for therapeutic intervention and treatment of disorders associated with aberrant tryptophan activity, or with aberrant cell metabolism or signal transduction, as described above. Other agents that increase or decrease tryptophan homeostasis (metabolism & uptake) activity or tryptophan levels associated with cellular functions may be developed into therapeutic products for the treatment of disorders associated with ligand binding activity.

As used herein, the term "multimer" refers to formation of a multimeric complex between two or more distinct molecules. The multimer complex may comprise, for example, two or more molecules of the same protein (e.g., a homo-dimer, -trimer, -tetramer or higher order multimer) or a mixture of two or more different (i.e., non-identical) proteins (e.g. a hetero-dimer, -trimer, -tetramer or higher multimer). For example, multimeric antibodies may comprise the same antibody or two or more different antibodies, each of which have two or more functions or activities (e.g., bind to two or more epitopes).

As used herein, the term "patient" or "subject" includes mammals (e.g., humans and animals).

As used herein, the term "RNAi construct" is a generic term used throughout the specification to include expression vectors (also referred to as RNAi expression vectors) capable of giving rise to transcripts which form dsRNAs or hairpin RNAs in cells, and/or transcripts which can produce siRNAs in vivo.

As used herein, the term "RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome.

As used herein, the term "variant" is intended to refer to polypeptides with at least about 70%, more preferably at least 75% identity, including at least 80%, 90%, 95% or greater identity to native molecules by BLAST analysis. Many such variants are known in the art, or can be readily prepared by random or directed mutagenesis of a native fluorescent molecules (see, for example, Fradkov et al., FEBS Lett. 479:127-130 (2000).

As used herein, the term, "plasmid" and "vector" are used interchangeably as the plasmid is the most commonly used form of vector. However, the invention is intended to include such other forms of expression vectors which serve equivalent functions and which become known in the art subsequently hereto. A vector may be any of a number of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

Vectors may further contain a promoter sequence. A promoter may include an untranslated nucleic acid sequence usually located upstream of the coding region that contains the site for initiating transcription of the nucleic acid. The promoter region may also include other elements that act as regulators of gene expression. In further embodiments of the invention, the expression vector contains an additional region to aid in selection of cells that have the expression vector incorporated. The promoter sequence is often bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes.

Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

An expression vector is one into which a desired nucleic acid sequence may be inserted by restriction and ligation such that it is operably joined or operably linked to regulatory sequences and may be expressed as an RNA transcript. Expression refers to the transcription and/or translation of an endogenous gene, transgene or coding region in a cell.

A coding sequence and regulatory sequences are operably joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

Some aspects of the present invention include the transformation and/or transfection of nucleic acids. Transformation is the introduction of exogenous or heterologous nucleic acid to the interior of a prokaryotic cell. Transfection is the introduction of exogenous or heterologous nucleic acid to the interior of a eukaryotic cell. The transforming or transfecting nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transfected cell is one in which the transfecting nucleic acid has become integrated into a chromosome so that it is inherited by daughter cells through chromosome replication. This stability is demonstrated by the ability of the eukaryotic cell to establish cell lines or clones comprised of a population of daughter cells containing the transfected nucleic acid.

As used herein, the term "fusion protein" or "chimeric protein" is used to refer to a polypeptide comprised of at least two polypeptides fused together either directly or with the use of spacer amino acids. The fused polypeptides may serve collaborative or opposing roles in the overall function of the fusion protein.

Biosensors

The present invention provides biosensors of multimeric ligand binding proteins for detecting and measuring changes in ligand concentrations using Fluorescence Resonance Energy Transfer (FRET). One embodiment, among others, is an isolated nucleic acid which encodes a fusion protein comprising a ligand binding fluorescent indicator; the indicator comprises at least one ligand binding protein moiety of a multimeric ligand binding protein complex, a donor fluorescent protein moiety covalently coupled to the ligand binding protein moiety, and an acceptor fluorescent protein moiety covalently coupled to the ligand binding protein moiety, wherein FRET between the donor moiety and the acceptor moiety is altered when the donor moiety is excited and ligand binds to the ligand binding protein moiety.

The isolated nucleic acid that encodes the multimeric ligand binding protein moiety can be any nucleic acid, and as an example, the nucleic acid that encodes portions of multimeric proteins. In one embodiment, the isolated nucleic acid of interest encodes a hetero- or, homo-dimer, -trimer, -tetramer, -pentamer, -hexamer or higher order multimer. Multimeric proteins may be selected, for example, from a binding protein (e.g. an antigen binding polypeptide), enzyme, receptor, ligand, nucleic acid binding protein (e.g. a repressor protein binding DNA), growth regulatory factor, differentiative factor, and chemotactic factor. For instance, the repressor protein, lac repressor, acts as a tetramer and the tyrosine repressor acts as a hexamer.

The invention provides isolated nucleic acids encoding tryptophan binding fluorescent indicators and the tryptophan fluorescent indicators encoded thereby. The embodiment, among others, is an isolated nucleic acid which encodes a tryptophan binding fluorescent indicator; the indicator comprises at least one tryptophan binding protein moiety of a multimeric ligand binding protein complex, a donor fluorescent protein moiety covalently coupled to the tryptophan binding protein moiety, and an acceptor fluorescent protein moiety covalently coupled to the tryptophan binding protein moiety, wherein FRET between the donor moiety and the acceptor moiety is altered when the donor moiety is excited and tryptophan binds to the tryptophan binding protein moiety.

As an example, the tryptophan binding protein moiety, among others, is a tryptophan binding protein moiety from *E. coli* having SEQ ID NO: 1.

Any portion of the tryptophan repressor DNA sequence which encodes a tryptophan binding region may be used in the nucleic acids of the present invention. Tryptophan binding portions of tryptophan binding protein (BP) or any of its homologues from other organisms, for instance Gram negative bacteria including thermophilic and hyperthermophilic organisms, may be cloned into the vectors described herein and screened for activity according to the disclosed assays. Ligand binding proteins of thermophilic and hyperthermophilic organisms are particularly useful for constructing sensors having increased stability and resistance to heat or harsh environmental conditions (See International Application PCT/US05/36954).

Naturally occurring species variants of tryptophan BP may also be used, in addition to artificially engineered variants comprising site-specific mutations, deletions or insertions that maintain measurable tryptophan binding function. Variant nucleic acid sequences suitable for use in the nucleic acid constructs of the present invention will preferably have at least 75, 80, 85, 90, 95 or 99% similarity or identity to the nucleotide sequence encoding tryptophan BP. Suitable variant nucleic acid sequences may also hybridize to the gene for tryptophan BP under highly stringent hybridization conditions. High stringency conditions are known in the art; see for example Sambrook et al., Molecular Cloning: A Laboratory Manual, 2d Edition, 1989, and Short Protocols in Molecular Biology, ed. Ausubel, et al. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Artificial variants of the present invention may be designed to exhibit decreased affinity for the ligand, in order to expand the range of ligand concentration that can be measured by the disclosed nanosensors. Additional artificial variants showing decreased or increased binding affinity for ligands may be constructed by random or site-directed mutagenesis and other known mutagenesis techniques, and cloned into the vectors described herein and screened for activity according to the disclosed assays. The binding specificity of disclosed biosensors may also be altered by mutagenesis so as to alter the ligand recognized by the biosensor (See, Looger et al., Nature, 423 (6936): 185-190).

The sensors of the invention may also be designed with tryptophan binding moieties and one or more additional protein binding moieties that are covalently coupled or fused together and to the donor and acceptor fluorescent moieties in order to generate an allosteric enzyme whose activity is controlled by more than one ligand. Allosteric enzymes containing dual specificity for more than one ligand have been described in the art, and may be used to construct the FRET biosensors described herein (Guntas and Ostermeier (2004) J. Mol. Biol. 336(1): 263-73).

As described herein, the donor and acceptor moieties may be fused to the termini of the at least one ligand binding moiety of a multimeric ligand binding protein complex or to an internal position within the at least one ligand binding moiety of a multimeric ligand binding protein complex so long as FRET between the donor moiety and the acceptor moiety is altered when the donor moiety is excited and a ligand binds to the ligand binding protein moiety (See International Application PCT/US05/36957).

The isolated nucleic acids of multimeric binding protein complex of the invention may comprise a structure according to the following formula (I):

A-B-C-D    (I)

wherein A and C are fluorophore moieties, and B and D are ligand binding protein moieties.

In one embodiment, the present invention provides an isolated nucleic acid, wherein said ligand binding fluorescent indicator comprises a structure of formula (I), wherein A and C are ligand binding protein moieties, and B and D are fluorophore moieties.

In another embodiment, the present invention provides an isolated nucleic acid, wherein said ligand binding fluorescent indicator comprises a structure of formula (I), wherein A and D are ligand binding protein moieties, and B and C are fluorophore moieties.

In yet another embodiment, the present invention provides an isolated nucleic acid, wherein said ligand binding fluorescent indicator comprises a structure of formula (I), wherein A and D are fluorophore moieties, and B and C are ligand binding protein moieties.

The ligand binding protein moieties may be from separate proteins of a multimeric ligand binding protein complex. Thus, the present invention provides an isolated nucleic acid with two or more polynucleotide moieties, each of which encodes a ligand binding protein that forms a part of the multimeric protein complex wherein the nucleic acid encodes a protein comprising a donor fluorophore moiety fused to the two or more ligand binding protein moieties, and an acceptor fluorophore moiety fused to the two or more ligand binding protein moieties.

The isolated nucleic acids of the invention may incorporate any suitable donor and acceptor fluorescent protein moieties that are capable in combination of serving as donor and acceptor moieties in FRET. Donor and acceptor moieties may be selected from the group consisting of GFP (green fluorescent protein), CFP (cyan fluorescent protein), BFP (blue fluorescent protein), OFP (orange fluorescent protein), RFP (red fluorescent protein), YFP (yellow fluorescent protein), and enhanced variants thereof such as enhanced YFP (EYFP), with a particularly preferred embodiment provided by the donor/acceptor pair CFP/YFP Venus, a variant of YFP with improved pH tolerance and maturation time (Nagai et al. (2002) Nat. Biotechnol. 20, 87-90). A variant of yellow fluorescent protein with fast and efficient maturation for cell-biological applications. An alternative is the MiCy/mKO pair with higher pH stability and a larger spectral separation (Karasawa et al. 2004). Also suitable as either a donor or acceptor is native DsRed from a *Discosoma* species, an ortholog of DsRed from another genus, or a variant of a native DsRed with optimized properties (e.g. a K83M variant or DsRed2 (available from Clontech)). Criteria to consider when selecting donor and acceptor fluorescent moieties is known in the art, for instance as disclosed in U.S. Pat. No. 6,197,928.

When the fluorophores of the biosensor contain stretches of similar or related sequence(s), the present inventors have recently discovered that gene silencing may adversely affect expression of the biosensor in certain cells and particularly whole organisms. In such instances, it is possible to modify the fluorophore coding sequences at one or more degenerate or wobble positions of the codons of each fluorophore, such that the nucleic acid sequences of the fluorophores are modified but not the encoded amino acid sequences. Alternatively, one or more conservative substitutions that do not adversely affect the function of the fluorophores may also be incorporated (See PCT Application No. PCT/US2005/036953).

It is also possible to use luminescent quantum dots (QD) for FRET (Clapp et al. (2005) J. Am. Chem. Soc. 127(4): 1242-50), dyes, including but not limited to TOTO dyes (Laib and Seeger (2004) J Fluoresc. 14(2):187-91), Cy3 and Cy5 (Churchman et al. (2005) Proc. Natl. Acad. Sci. U.S.A. 102 (5): 1419-23), Texas Red, fluoresce in, and tetramethylrhodamine (TAMRA), as well as fluorescent tags (See, Hoffman et al. (2005) Nat. Methods 2(3): 171-76). Other luminescent reporters may also be utilized, such as luciferase and renilla and derivatives thereof.

The invention further provides for the fusion of other isolated nucleotides fused to the isolated nucleotides described above. The fused nucleotides may encode other polypeptide domains useful for binding or targeting the expressed fusion protein. By way of example, targeting sequences may include nuclear localization sequences, excretion sequences and plasma membrane sequences, so that the resulting fusion protein is located in the nucleus, the nucleolus, vacuoles, the endoplasmic reticulum, bound to either the inside or outside of the plasma membrane or secreted from the cell into the extracellular space.

The invention further provides vectors containing isolated nucleic acid molecules encoding the biosensor polypeptides described herein. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. Such vectors include expression vectors containing expression control sequences operatively linked to the nucleic acid sequence coding for the biosensor. Vectors may be adapted for function in a prokaryotic cell, such as *E. coli* or other bacteria, or a eukaryotic cell, including animal cells or plant cells. For instance, the vectors of the invention will generally contain elements such as an origin of replication compatible with the intended host cells, one or more selectable markers compatible with the intended host cells and one or more multiple cloning sites. The choice of particular elements to include in a vector will depend on factors such as the intended host cells, the insert size, whether regulated expression of the inserted sequence is desired, i.e., for instance through the use of an inducible or regulatable promoter, the desired copy number of the vector, the desired selection system, and the like. The factors involved in ensuring compatibility between a host cell and a vector for different applications are well known in the art.

Preferred vectors for use in the present invention will permit cloning of the tryptophan binding domain or receptor between nucleic acids encoding donor and acceptor fluorescent molecules, resulting in expression of a chimeric or fusion protein comprising the tryptophan binding domain covalently coupled to donor and acceptor fluorescent molecules. Exemplary vectors include the bacterial pFLIP derivatives disclosed in Fehr et al. (2002) Proc. Natl. Acad. Sci. USA 99, 9846-9851. Methods of cloning nucleic acids into vectors in the correct frame so as to express a fusion protein are well known in the art.

The tryptophan biosensors of the present invention may be expressed in any location in the cell, including the cytoplasm, cell surface or subcellular organelles such as the nucleus, vesicles, endoplasmic reticulum (ER), vacuole, etc. Methods and vector components for targeting the expression of proteins to different cellular compartments are well known in the art, with the choice dependent on the particular cell or organism in which the biosensor is expressed. (See, Okumoto et al. (2005) Proc. Natl. Acad. Sci. USA 102:8740-8745; Fehr et al. (2004) J. Fluoresc. 14:603-609). Furthermore, expression of the tryptophan biosensors may be placed under the regulatory control of an inducible promoter The chimeric nucleic acids of the present invention may be constructed such that the donor and acceptor fluorescent moiety coding sequences are fused to separate termini of the ligand binding domain in a manner such that changes in FRET between donor and acceptor may be detected upon ligand binding. Fluorescent domains can optionally be separated from the ligand binding domain by one or more flexible linker sequences. Such linker moieties are preferably between about 1 and 50 amino acid residues in length, and more preferably between about 1 and 30 amino acid residues. Linker moieties and their applications are well known in the art and described, for example, in U.S. Pat. Nos. 5,998,204 and 5,981,200, and Newton et al., Biochemistry 35:545-553 (1996). Alternatively, shortened versions of linkers or any of the fluorophores described herein may be used. For example, the inventors have shown that deleting N- or C-terminal portions of any of the three modules can lead to increased FRET ratio changes, as described in U.S. Patent Application No. 60/658,141.

It will also be possible depending on the nature and size of the ligand binding domains to insert one or both of the fluorescent molecule coding sequences within the open reading frames of the binding proteins such that the fluorescent moieties are expressed and displayed from a location within the biosensor rather than at the termini. Such sensors are generally described in U.S. Patent Application No. 60/658,141. It will also be possible to insert a ligand binding sequence into a single fluorophore coding sequence, i.e. a sequence encoding a GFP, YFP, CFP, BFP, etc., rather than between tandem molecules. According to the disclosures of U.S. Pat. No. 6,469,154 and U.S. Pat. No. 6,783,958, such sensors respond by producing detectable changes within the protein that influence the activity of the fluorophore.

Host cells may be transfected with a vector or an expression vector of the invention, including prokaryotic cells, such as E. coli or other bacteria, or eukaryotic cells, such as yeast cells, animal cells or plant cells. In another aspect, a transgenic non-human animal may have a phenotype characterized by expression of the nucleic acid sequence coding for the expression of the environmentally stable biosensor. The phenotype is conferred by a transgene contained in the somatic and germ cells of the animal, which may be produced by (a) introducing a transgene into a zygote of an animal, the transgene comprising a DNA construct encoding the tryptophan biosensor; (b) transplanting the zygote into a pseudopregnant animal; (c) allowing the zygote to develop to term; and (d) identifying at least one transgenic offspring containing the transgene. The step of introducing of the transgene into the embryo can be achieved by introducing an embryonic stem cell containing the transgene into the embryo, or infecting the embryo with a retrovirus containing the transgene. Transgenic animals of the invention include transgenic C. elegans and transgenic mice and other animals. Transgenic plants are also included.

Host cells may include any transfectable cell line that is primary, immortalized or established. By way of example established host cells may include KB (human squamous cell carcinoma) (ATCC CCL 17); 293 (human embryonic kidney) (ATCC CRL-1573); 293F (Invitrogen, Carlsbad Calif.); 293T and derivative 293T/17 (293tsA1609neo and derivative ATCC CRL-11268) (human embryonic kidney transformed by SV40 T antigen); COS-7 (monkey kidney CV1 line transformed by SV40) (ATCC CRL1651); BHK (baby hamster kidney cells) (ATCC CRLIO); CHO (Chinese hamster ovary cells); mouse Sertoli cells; CV1 (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

The present invention employs isolated biosensor molecules having the properties described herein, particularly tryptophan binding fluorescent indicators. Such polypeptides may be recombinantly expressed using the nucleic acid constructs described herein, or produced by chemically coupling some or all of the component domains. The expressed polypeptides can optionally be produced in and/or isolated from a transcription-translation system or from a recombinant cell, by biochemical and/or immunological purification methods known in the art. The polypeptides of the invention can be introduced into a lipid bilayer, such as a cellular membrane extract, or an artificial lipid bilayer (e.g. a liposome vesicle) or nanoparticle. The isolated biosensors may further be fused to a tag to aid purification. By way of example, the tag may be a His-tag, a myc-tag, an S-peptide tag, a MBP tag (maltose binding protein), a GST tag (glutathione S-transferase), a FLAG tag, a thioredoxin tag, a GFP tag (green fluorescent protein), a BCCP (biotin carboxyl carrier protein), a calmodulin tag, a Strep tag, an HSV-epitope tag, a V5-epitope tag, and a CRP tag. The use of such epitopes and affinity tags is known to those skilled in the art.

Methods of Detecting and Monitoring Tryptophan and Tryptophan/Kynurenine Exchange In one aspect, the present invention provides methods for the rapid and efficient detection of tryptophan using a biosensor of multimeric tryptophan binding moieties. The binding partner can be monovalent, bivalent or polyvalent. Thus, the biosensor nucleic acids and proteins of the present invention are useful for detecting tryptophan binding and measuring changes in the levels of tryptophan both in vitro and in a plant or a subject in vivo and ex vivo.

The present invention provides methods for monitoring tryptophan movement across the plasma membrane. The present invention provides that tryptophan concentrations can be affected by amino acid transporters, such as the L-amino acid transporter types 1 and 2 (LAT-1 and LAT-2). The present invention also provides that intercellular levels and intracellular levels of tryptophan may be modulated by the concentration of L-amino acids in the extracellular space of the cell.

By way of example, perfusing cells with high concentrations of L-amino acids may deplete internal tryptophan concentrations. By way of further example, perfusing cells with L-tryptophan will increase internal levels of tryptophan. The present invention also provides that perfusing can establish a calibration curve to determine the tryptophan level in a cell. Affinity constants ($K_d$) may be determined by fitting the titration curves to a single-site-binding isotherm: $R=R_{apo}+(R_{sat}-R_{apo})\cdot(n\cdot[L])/(K_d+[L])$ with [L], ligand concentration; n, number of equal binding sites; R, ratio; $R_{apo}$, ratio in the absence of ligand; and $R_{sat}$, ratio at saturation with ligand.

The invention comprises a method of detecting changes in the level of tryptophan in a sample of cells, comprising (a) providing a cell expressing a nucleic acid encoding a tryptophan biosensor as described herein and a sample of cells; and (b) detecting a change in FRET between a donor fluorescent protein moiety and an acceptor fluorescent protein moiety, each covalently attached to the tryptophan binding domain, wherein a change in FRET between said donor moiety and said acceptor moiety indicates a change in the level of tryptophan in the sample of cells.

Detection of modulations in tryptophan concentrations is also provided in the present invention. Accordingly, the changes in FRET between multiple points in time can be measured and the cumulative changes to tryptophan levels can be measured and collected.

The present invention also provides a method for monitoring the exchange of tryptophan for its metabolites, kynurenine, formyl kynurenine, and 3-hydroxy kynurenine. The present invention provides that kynurenine may be present in a cell in response to tryptophan metabolism, or in response to exchange with tryptophan through a L-amino acid transporter, such as LAT-1 and LAT-2.

The present invention further provides methods for expressing a L-amino acid transporter into a cell. In some embodiments, the L-amino acid transporter is expressed by introducing a vector into a cell, wherein the vector is comprised of a nucleic acid encoding a L-amino acid transporter operably linked to a promoter. In one embodiment, the L-amino acid transporter is LAT-1 or LAT-2. The nucleotide and amino acid sequences of LAT-1 and LAT-2 are known in the art for multiple species, as are various functional mutants. By way of example, protein accession numbers BAB7078, CAA95945, AAD20464, CAJ58680, AAN85315, BAA90956, AAB93541, and AAF20380, as well as nucleotide accession numbers NP 003477, NP 035534, NP 001083534, NP 036376, NP 058668, and AY162432.

The present invention also provides methods for expressing an enzyme to metabolize tryptophan to kynurenine, such as indoleamine 2,3-dioxygenase (IDO). The enzyme may be expressed by introducing a vector into a cell, wherein the vector comprises a nucleic acid encoding the enzyme operably linked to a promoter. The nucleotide sequences for IDO are known in the art for multiple species, as are various functional variants. By way of example, nucleotide accession numbers NP 002155, NP 032350, and NP 076463.

FRET may be measured using a variety of techniques known in the art. For instance, the step of determining FRET may comprise measuring light emitted from the acceptor fluorescent protein moiety. Alternatively, the step of determining FRET may comprise measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety. The step of determining FRET may also comprise measuring the excited state lifetime of the donor moiety or anisotropy changes (Squire et al. (2004) J. Struct. Biol. 147(1):62-9. Red-edge anisotropy microscopy enables dynamic imaging of homo-FRET between green fluorescent proteins in cells.). Such methods are known in the art and described generally in U.S. Pat. No. 6,197,928.

The amount of tryptophan and its analogs in a sample of cells can be obtained by determining the concentration, degree, or level of FRET. First the sensor must be introduced into the sample. Changes in tryptophan concentration can be determined by monitoring FRET at a first and second time after contact between the sample and the fluorescent indicator and determining the difference in the degree of FRET. The amount of tryptophan in the sample can be quantified for example by using a calibration curve established by titration.

The cell sample to be analyzed by the methods of the invention may be contained in vivo, for instance in the measurement of tryptophan transport or signaling on the surface of cells, or in vitro, wherein tryptophan efflux may be measured in cell culture. Alternatively, a fluid extract from cells or tissues may be used as a sample from which tryptophan is detected or measured.

Methods for detecting tryptophan levels as disclosed herein may be used to screen and identify compounds that may be used to modulate tryptophan concentrations and activities relating to tryptophan changes. In one embodiment, among others, the invention comprises a method of identifying a compound that modulates tryptophan homeostasis (metabolism & uptake) or levels comprising (a) contacting a mixture comprising a cell expressing a tryptophan biosensor as disclosed herein and a sample of cells with one or more test compounds, and (b) determining FRET between said donor fluorescent domain and said acceptor fluorescent domain following said contacting, wherein increased or decreased FRET following said contacting indicates that said test compound is a compound that modulates tryptophan binding activity or tryptophan levels.

In addition to detection of tryptophan through the use of biosensors, other methods known in the art for detecting and quantitating the levels, both intracellularly and extracellularly, of tryptophan and its metabolites, such as kynurenine and 3-hydroxy kynurenine, may be utilized. By way of example, tryptophan and kynurenine may be detected and quantitated by chromatography, such as high performance liquid chromatography. Tryptophan and kynurenine may further be detected and quantitated through the use of radiolabeling, spectrophotometry, coulometry, fluorescence, chemoluminescence, antibody binding, electro-chemical sensors, and nuclear magnetic resonance spectrophotometry.

Methods of Treatment

The present invention includes methods for treating a disease associated with immunosuppression in a subject in need thereof comprising, contacting the subject with or administering to the subject a therapeutically effective amount of at least one agent that modulates coupled counterexchange of tryptophan for kynurenine or a catabolite of kynurenine across a cell membrane. In one embodiment, the agent decreases or prevents the coupled counterexchange of tryptophan for kynurenine or a degradation product of kynurenine. The decrease in the coupled counterexchange of tryptophan for kynurenine or a degradation product of kynurenine maybe at least about below 90% and for example about 100% below, that observed in the subject prior to treatment. In another embodiment, the agent increases the coupled counterexchange of tryptophan for kynurenine or a degradation product of kynurenine. The increase in the coupled counterexchange of tryptophan for kynurenine or a degradation product of kynurenine may be about at least about above 90% and for example 100% above, that observed in the subject prior to treatment.

In some embodiments, the subject is an animal. In further embodiments, the animal is a human.

In some embodiments, the disease may be cancer. It is known in the art that some cancers may affect the immune system of a subject. Cancer cells may suppress the immune system of a subject. By way of example, a cancer may cause increased production of kynurenine.

In other embodiments, the disease may be selected from the group consisting of autoimmune disease and inflammatory disease. Autoimmune diseases include diabetes mellitus type 1, systemic lupus erythematosus, celiac disease, Crohn's disease, multiple sclerosis, rheumatoid arthritis, Sjögren's syndrome, Hashimoto's thyroiditis, Goodpasture's syndrome, Guillain-Barré syndrome, Kawasaki's disease, myasthenia gravis, opsoclonus myoclonus syndrome, idiopathic thrombocytopenic purpura, primary biliary cirrhosis, Reiter's syndrome, Addison's disease, acute disseminated encephalomyelitis, Ankylosing spondylitis, aplastic anemia, autoimmune hepatitis, oophoritis, gestational pemphigoid, optic neuritis, Ord's thyroiditis, pemphigus, Gaucher's disease, pernicious anemia, Takayasu's arteritis, and Wegener's granulomatosis.

The present invention provides methods to regulate immunosuppression. In some embodiments, immunosuppression may be regulated through affecting the tryptophan\kynurenine exchange, such as affecting the LAT-1 and LAT-2 transporters. In other embodiments, immunosuppression may be regulated by affecting kynurenine production, such as by affecting IDO. In some embodiments, it may be desirable to depress the level of immunopsuppression. In other embodiments is may be desirable to increase immunosuppression. By way of example, increasing immunosuppression may prevent rejection of a transplant, a graft, or an implant. By way of example, the present invention may regulate a subject's immune response to a synthetic limb, organ, bone, valve, or joint. The present invention may also regulate a subject's immune response to the introduction of cell's from another. By way of example, the present invention may regulate a subject's immune response to a heart transplant, liver transplant, lung transplant, skin graft, face transplant, face graft, eye transplant, kidney transplant, hair transplant, pancreas transplant, intestine transplant (small or large), hand transplant, cornea transplant, bone marrow transplant, stem cell implant, blood transfusion, penis transplant, and islet of Langerhans transplant. Rejection may also include responses to microchimerism. Microchimerism may refer to a small number of cells present in a subject that originate from another subject. Rejection may further apply to regions that are considered to be immune privileged, such as the eyes, brain, testes, and uterus.

The present invention may further provide methods to regulate immune responses generated by and during pregnancy. These may include reactions to an embryo by the mother, such as allogenic fetal rejection and Rh factor incompatibility. These may also include an embryo or fetus's incompatibility with the mother, such as in Erythroblastosis Fetalis. These may further include postpartum autoimmune responses, such as those listed above, and may be caused by conditions such as fetal microchimerism. Fetal microchimerism refers to cells from the fetus passing into the mother.

In one embodiment, the agent that treats a disease involving immunosuppression may be identified by the method of the present invention, comprising:

(a) measuring tryptophan concentration at a location in the disease using a tryptophan fluorescence resonance energy transfer (FRET) nanosensor;
(b) applying the agent to the disease; and
(c) subsequently measuring tryptophan concentration at the same location as in (a) in the disease using a tryptophan FRET nanosensor, wherein a change in the tryptophan concentration in (c) compared to the tryptophan concentration in (a) is indicative of an agent that modulates immunosuppression. A location in the disease may include the disease site, or a biological sample comprising cells or tissue.

For the purposes of the present invention, the agent may be introduced into a subject either ex vivo, (i.e., in a cell or cells removed from the subject) or directly in vivo into the body to be treated.

In one particular class of embodiments, the agent is introduced into a subject for purposes of therapy. Gene therapy provides methods for combating chronic infectious diseases such as HIV, as well as non-infectious diseases such as cancer and birth defects such as enzyme deficiencies.

In some embodiments, the present invention relates to methods of treating a subject that has a disease associated with immunosuppression, in which inhibition of coupled counterexchange of tryptophan for kynurenine or its degradation product are desired. In other embodiments, the invention provides methods of treating a subject that has a disease associated with immunosuppression in which an increase in the coupled counterexchange of tryptophan for kynurenine or its degradation product is desired. These methods may be accomplished by removing the diseased site from a subject and introducing a nucleic acid into an appropriate vector, which is subsequently introduced into the diseased site or contacting the diseased site with a chemical. Alternatively, a subject may be directly treated with an appropriate nucleic acid or chemical that modulates coupled counterexchange of tryptophan for kynurenine or its degradation product.

In another embodiment, cells can be removed from a subject having a disease associated with immunosuppression, and then a nucleic acid is introduced into the cell. These transfected cells will thereby produce functional protein or fragments thereof from the nucleic acid and can be reintroduced into the patient. Methods described in U.S. Pat. No. 5,162,215 (Bosselman et al.) demonstrate how to detect the presence and expression of a nucleic acid. Methods described in U.S. Pat. No. 5,741,486 (Pathak et al.) teach the use of viral vectors in gene therapy. These methods can be used to introduce agents into one or more cells that are capable of modulating the coupled counterexchange of tryptophan for kynurenine or its degradation products. A nucleic acid may be introduced into a cell for the purposes of increasing tryptophan metabolism. Such nucleic acids may encode a functional indoleamine 2,3-dioxygenase (IDO). Other nucleic acids may be introduced into a cell to inhibit the coupled counterexchange of tryptophan with kynurenine or its degradation products. Such nucleic acids may comprise RNAi and may be specific for the LAT-1 and/or LAT-2 amino acid counter-exchanger.

In some embodiments, the nucleic acid can be introduced into a subject in vivo. The scientific and medical procedures required for human cell transfection are now routine procedures. Administration is by any of the routes normally used for introducing a molecule into cells. The packaged nucleic acids are administered in any suitable manner, preferably with pharmaceutically acceptable carriers. Suitable methods of administering such packaged nucleic acids in the context of the present invention to a subject are available, and although more than one route can be used to administer a particular composition, a particular route can often provide a more immediate and more effective reaction than another route.

The agents may be administered to a subject as solutions or suspensions. Injection solutions and suspensions can be prepared from sterile powders, granules, and tablets of the kind previously described. Cells transduced by the packaged nucleic acid as described above in the context of ex vivo therapy can also be administered intravenously or parenterally as described above. The dose administered to a subject, in the context of the present invention should be sufficient to effect a beneficial therapeutic response in the subject over time, or to inhibit infection by a pathogen. The dose will be determined by the efficacy of the particular transgene employed and the condition of the subject, as well as the body weight or surface area of the subject to be treated. The size of the dose also will be determined by the existence, nature, and extent of any adverse side-effects that accompany the administration of a particular vector, or transduced cell type in a particular subject.

In determining the effective amount agent to be administered in the treatment of a disease, the physician or other clinician evaluates symptom or clinical parameters, including the progression of the disease. In general, the dose equivalent of a naked nucleic acid from a vector is from about 1 µg to 100 µg for a typical 70 kilogram. The exact dosage of agent is dependent upon a variety of factors, including the age, weight, and sex of the subject to be treated, and the nature and extent of the disease or disorder to be treated. Effective doses can be extrapolated from dose-response curves derived from in vitro or animal model test systems.

Administration can be accomplished via single or divided doses. Methods of introduction include, but are not limited to, intradermal, intramuscular, intraperitoneal, intravenous, subcutaneous, intranasal, and oral routes. Administration can be by any convenient route, for example by infusion or bolus injection, by absorption through epithelial or mucocutaneous linings (e.g., oral mucosa, rectal and intestinal mucosa, etc.). In addition, the pharmaceutical compositions can be introduced into the central nervous system by any suitable route, including intraventricular and intrathecal injection; intraventricular injection can be facilitated by an intraventricular catheter, for example, attached to a reservoir, such as an Ommaya reservoir. Administration can be systemic or local. The agents can be administered together with other biologically active agents.

In some of the foregoing embodiments, it may only be necessary to introduce the genetic or protein elements into only certain cells or tissues. However, in some instances (i.e. tumors), it may be more therapeutically effective and simple to treat all of the patients cells, or more broadly disseminate the vector, for example by intravascular administration.

In another embodiment, ex vivo methods for introducing an agent into a subject involve transducing the cell ex vivo, and then subsequently introducing the cell into the subject. Transduced cells are prepared for reinfusion according to established methods (See, Abrahamsen et al. (1991) J. Clin. Apheresis 6:48-53; Carter et al. (1988) J. Clin. Apheresis 4:113-117; Aebersold et al. (1988) J. Immunol. Methods 112: 1-7; Muul et al. (1987) J. Immunol. Methods 101: 171-181; and Carter et al. (1987) Transfusion 27:362-365).

Methods of Identifying Agents that Modulate Tryptophan, Tryptophan/Kynurenine Exchange, and Immunosuppression The present invention provides methods for identifying an agent that modulates tryptophan concentration in a cell, comprising providing the cell with the tryptophan biosensors disclosed herein, obtaining a first FRET measurement, applying a test agent, and then obtaining a second FRET measurement, wherein a change in the FRET is indicative of the agent modulating tryptophan levels. In some embodiments, the extracellular level of tryptophan is also monitored.

In some embodiments, the agent may increase tryptophan levels in the cell. In other embodiments, the agent may decrease or deplete tryptophan levels in the cell. The cell may be in a biological sample. The biological sample may be a biological fluid or tissue. Biological fluids may include sweat, blood, urine, semen, biopsy fluid, bile, breast milk, and saliva. The biological sample may be from a subject. The agent may modulate tryptophan levels by affecting tryptophan metabolism, either directly or indirectly. For example, the agent may inhibit IDO. The agent may also stimulate IDO activity. The agent may also or alternatively modulate tryptophan levels by affecting tryptophan transport, such as by affecting LAT-1 or LAT-2. The agent may further be a system L inhibitor, such as BCH.

The present invention also provides methods for identifying agents that modulate tryptophan/kynurenine exchange in a cell, comprising providing the cell with the tryptophan biosensors disclosed herein, obtaining a first FRET measurement, applying a test agent, and then obtaining a second FRET measurement, wherein changes in the FRET measurements are indicative that the agent modulates tryptophan/kynurenine exchange. In some embodiments, the level of kynurenine may also be obtained, either internal of the cell, or extracellular. In other embodiments, the extracellular level of tryptophan may be obtained.

The agent may affect tryptophan/kynurenine exchange by affecting tryptophan metabolism to kynurenine. In one aspect of the invention, the agent will increase metabolism, thereby increasing kynurenine levels. In another aspect of the invention, the agent will decrease tryptophan metabolism, thereby relatively decreasing kynurenine. The agent may act directly or indirectly on tryptophan metabolism. The agent may affect IDO activity in particular.

The agent may affect tryptophan/kynurenine exchange by affecting a tryptophan/kynurenine exchanger, such as a L-amino acid transporter. In some embodiments, the tryptophan/kynurenine transporter is LAT-1 or LAT-2. The agent may act directly or indirectly on the tryptophan/kynurenine exchanger. In some embodiments, the agent will increase the activity of the transporter so that the rate is faster. In other embodiments, the agent may affect the transporter so that the transporter's ability to regulate exchange is modulated. Moreover, the agent may inhibit, partially or completely, the ability to exchange tryptophan and kynurenine. The agent may be a system L inhibitor, such as BCH.

The agent may affect the metabolism of tryptophan to kynurenine. In certain embodiments, the agent may affect the enzymatic activity of IDO to regulate kynurenine production. In other embodiments, the agent is a cytokine, may be interferon-γ, (IFN-γ). Those skilled in the art will recognize that agents modulating a cytokine receptor can exacerbate or enhance the effect of administering the cytokine. Those skilled in the art will further recognize that modulating a cytokine receptor may substitute for administering the cytokine itself.

The present invention provides methods for identifying at least one agent that modulates a disease involving immunosuppression, comprising: (a) measuring tryptophan concentration at a location in the disease using a tryptophan fluorescence resonance energy transfer (FRET) nanosensor; (b) applying the agent to the disease; and (c) subsequently measuring tryptophan concentration at the same location as in (a) in the disease using a tryptophan FRET nanosensor, wherein a change in the tryptophan concentration in (c) compared to the tryptophan concentration in (a) is indicative of an agent that modulates immunosuppression. A location in the disease may include the disease site, or a biological sample comprising cells or tissue.

In one embodiment, high throughput screening methods may be used to identify agents that can modulate the tryptophan levels or the metabolism of tryptophan or the coupled counterexchange of tryptophan and kynurenine or its metabolite or degradation products. Such methods may involve providing a combinatorial chemical or peptide library containing a large number of potential therapeutic compounds (potential modulator or ligand compounds). Combinatorial chemical libraries are then screened in one or more assays, as described herein, to identify those library members (particular chemical species or subclasses) that display a desired characteristic activity, i.e. modulate the coupled counterexchange of tryptophan for kynurenine or its degradation products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka (1991) Pept. Prot. Res. 37:487-493 and Houghton et al. (1991) Nature 354:84-88). Other chemistries for generating chemical diversity libraries can also be used. Such chemistries include, but are not limited to peptides (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al. (1993) Proc. Nat. Acad. Sci. USA 90:6909-69 13), vinylogous polypeptides (Hagihara et al. (1992) J. Amer. Chem. Soc. 114:6568), nonpeptidal peptidomimetics with glucose scaffolding (Hirschmann et al. (1992) J. Amer. Chem. Soc. 114:9217-9218), analogous organic syntheses of small compound libraries (Chen et al. (1994) J. Amer. Chem. Soc. 116:2661), oligocarbamates (Cho et al. (1993) Science 261:1303), and/or peptidyl phosphonates (Campbell et al. (1994) J. Org. Chem. 59:658), nucleic acid libraries (see, Ausubel, Berger and Russell & Sambrook), peptide nucleic acid libraries (see, e.g., U.S. Pat. No. 5,539,083), antibody libraries (see, e.g., Vaughn et al. (1996) Nature Biotechnology, 14(3):309-314 and PCT/US96/10287), carbohydrate libraries (see, e.g., Liang et al. (1996) Science, 274:1520-1522 and U.S. Pat. No. 5,593,853), small organic molecule libraries (see, e.g., benzodiazepines, Baum C& EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514).

Devices for the preparation of combinatorial libraries are commercially available. In addition, numerous combinatorial libraries are themselves commercially.

Alternatively, an RNAi library may be screened to ascertain the identity of agents (RNAi molecules) that modulate the coupled counterexchange of tryptophan for kynurenine or its degradation products. Mammalian siRNA and shRNA libraries have been used successfully to screen for those siRNAs that are capable of modulating a cellular pathway, function or response (Berns et al. (2004) Nature 428:431-437; Kittler et al. (2004) Nature 432:1036-1040; Kolfschoten et al. (2005) Cell 121:849-858; Paddison et al. (2004) Nature 428: 427-431; Pelkmans et al. (2005) Silva et al. (2005) Nat. Genet. 37:1281-1288; Westbrook et al. (2005) Cell 121:837-848; and Moffat et al. (2006) Cell 124:1286-1298). Such RNAi libraries may then be transfected and expressed within a cell or population of cells according to standard protocols.

RNAi constructs from an RNAi library may comprise double stranded RNA that can specifically block expression of a target gene. Accordingly, RNAi constructs can act as antagonists by specifically blocking expression of a particular gene. "RNA interference" or "RNAi" is a term initially applied to a phenomenon observed in plants and worms where double-stranded RNA (dsRNA) blocks gene expression in a specific and post transcriptional mariner.

The RNAi constructs contain a nucleotide sequence that hybridizes under physiologic conditions of the cell to the nucleotide sequence of at least a portion of the mRNA transcript for the gene to be inhibited (i.e., the 'target' gene). The double-stranded RNA need only be sufficiently similar to natural RNA that it has the ability to mediate RNAi. Thus, the invention has the advantage of being able to tolerate sequence variations that might be expected due to genetic mutation, strain I polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Homology or sequence identity at the nucleotide or amino acid sequence level is determined by BLAST (Basic Local Alignment Search Tool) analysis using the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over eighty-five nucleotides or amino acids in length.

For blastn, the scoring matrix is set by the ratios of M (i.e., the reward score for a pair of matching residues) to N (i.e., the penalty score for mismatching residues), wherein the default values for NI and N are +5 and −4, respectively. Four blastn parameters were adjusted as follows: Q=10 (gap creation penalty); R=10 (gap extension penalty); wink=1 (generates word hits at every wink position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis. Methods of chemically modifying RNA molecules can be adapted for modifying RNAi constructs (see, for example, Heidenreich et al. (1997) Nucleic Acids Res, 25:776-780; Wilson et al. (1994) J. Mol. Recog. 7:89-98; Chen et al. (1995) Nucleic Acids Res 23:2661-2668; Hirschbein et al. (1997) Antisense Nucleic Acid Drug Dev 7: 55-6 1). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a configuration).

The double-stranded structure may be formed by a single self complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNA are double stranded, and may include short overhangs at each end.

The overhangs may be 1-6 nucleotides in length at the 3' end. It is known in the art that the siRNAs can be chemically synthesized, or derived from a longer double-stranded RNA or a hairpin RNA. The siRNAs have significant sequence similarity to a target RNA so that the siRNAs can pair to the target RNA and result in sequence-specific degradation of the target RNA through an RNA interference mechanism. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc. Natl. Acad. Sci. U.S.A., 98:9742-9747; Elbashir, et al. (2001) EMBO J. 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography; (e.g., size exclusion chromatography), glycerol gradient centrifugation, affinity purification with antibody can be used to purify siRNAs. In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2' deoxythymidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (i.e., hairpin RNA). The hairpin RNAs can be synthesized exogenously or can be fat ined by transcribing from RNA polymerase III promoters in vivo.

Examples of making and using such hairpin RNAs for gene silencing in mammalian cells are described in, for example, Paddison et al. (2002) Series Dev 16:948-58; McCaffrey et al. (2002) Nature 418:38-9; McManus et al. (2002) RNA 8:842-50; Yu et al. (2002) Proc. Natl. Acad. Sci. U.S.A. 99: 6047-52). Preferably, such hairpin RNAs are engineered in cells or in an animal to ensure continuous and stable suppression of a desired gene. It is known in the art that siRNAs can be produced by processing a hairpin RNA in the cell. In yet other embodiments, a plasmid is used to deliver the double-stranded RNA, e.g., as a transcriptional product. In such embodiments, the plasmid is designed to include a coding sequence for each of the sense and antisense strands of the RNAi construct. The coding sequences can be the same sequence, e.g., flanked by inverted promoters, or can lie two separate sequences each under transcriptional control of separate promoters. After the coding sequence is transcribed, the complementary RNA transcripts base-pair to form the double stranded RNA.

WO 01/77350 describes an exemplary vector for directional (or convergent) transcription of a transgene to yield both sense and antisense RNA transcripts of the same transgene in a eukaryotic cell. Accordingly, in certain embodiments, the present invention provides a recombinant vector having the following unique characteristics, it comprises a viral replicon having two overlapping transcription units arranged in an opposing orientation and flanking a transgene for an RNAi construct of interest, wherein the two overlapping transcription units yield both sense and antisense RNA Transcripts from the same transgene fragment in a host cell (see Tran et al. (2003) BMC Biotechnology 3:21, which is herein incorporate by reference in its entirety).

Pharmaceutical Compositions

The present invention provides methods for treating a disease associated with immunosuppression in a subject in need thereof comprising, contacting the subject effected by the disease or administering to cells obtained from the subject an agent that modulates the coupled counterexchange of tryptophan for kynurenine or its metabolic products. The pharmaceutical composition or formulation may comprise one or more agents selected from the group consisting of a genomic RNAi library and a chemical library. In one embodiment, the RNAi library is contained in an appropriate expression vector. In yet another embodiment, the RNAi is contained within a liposome.

Various delivery systems are known and can be used to administer a pharmaceutical composition useful for treating a disease associated with immunosuppression, e.g., encapsulation in liposomes, microparticles, microcapsules, recombinant cells capable of expressing the mutant viruses, receptor mediated endocytosis (see e.g., Wu et al. (1987) J. Biol. Chem. 262, 4429-4432). Methods of introduction include but are not limited to intradermal, intramuscular, intraperitoneal, intravenous, subcutaneous, intranasal, epidural, sublingual, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In a preferred embodiment, it may be desirable to introduce the pharmaceutical compositions of the invention into the affected tissues by any suitable route. Pulmonary administration can also be employed, e.g., by use of an inhaler or nebulizer, and formulation with an aerosolizing agent. It is further possible to administer the agents through encapsulation in liposomes.

As mentioned above for some methods of the invention, topical administration may be used. Any common topical formulation such as a solution, suspension, gel, emulsion, ointment or salve and the like may be employed. Preparation of such topical formulations are described in the art of pharmaceutical formulations as exemplified, for example, by Gennaro et al. (2005) Remington's Pharmaceutical Sciences, Mack Publishing. For topical application, the compositions could also be administered as a powder or spray, particularly in aerosol form. In one embodiment, the compositions of this invention may be administered by inhalation. For inhalation therapy, the active ingredients may be in a solution useful for administration by metered dose inhalers or in a form suitable for a dry powder inhaler. In another embodiment, the compositions are suitable for administration by bronchial lavage.

It may be desirable to administer the pharmaceutical compositions capable of treating a disease associated with immunosuppression locally to the area in need of treatment by routes well-known to one of skill in the art, including actinal, rectal, dialysis membrane, or enteric administration; extragastrointestinal administration including intramuscular, hypodermal, intramedullary, introthecal, directly intraventricular, intravenous, intraperitoneal, intranasal, or intraocular injection; percutaneous, local, sublingual, vaginal administration, etc. The dosage formulations include (but not limited to) tables, pastille, powders, suspensions, suppositories, solution, capsules, frost, plasters, and micro-motors. For convenience, the drug combinations of the present invention can be made up by routine methods into any pharmacologically acceptable formulation using one or more physiologically acceptable carriers. The drug combinations of the present invention can comprise one or more excipient and adjuvant to facilitate the processing of active compounds. The formulation is determined by the administration route. To facilitate the injection, the peptides or combinations of present invention can be prepared as a solution, e.g., a physiological saline solution. In the case of dialysis membrane administration, penetrants that facilitate the preparation penetration of barriers should be used, and these penetrants should be generally known in this field.

The oral dosage formulation of the pharmaceutical compositions capable of treating a disease associated with immunosuppression can be ground together with solid excipients into a well-distributed mixture and then processed into granules that are further processed into tablets or the kernel of sugar-coated tablets; if necessary, proper adjuvant can be added to the mixture. Proper excipients and fillers can be sugar, such as lactose, saccharose, mannitol, or sorbicolan; fibrin products, such as cornstarch, wheaten starch, rice starch, potato starch, glutin, tragacanth, methyl cellulose, hydroxypropylmethyl cellulose, sodium carboxymethyl cellulose, and/or polyvinylpyrrolidone. If necessary, disintegrants, such as cross-linked polyvinylpyrrolidone, agar, alginic acid, or its salt-like alginate sodium. Proper coat should be provided to the kernel of sugar-coated tablets. The coat can be made from concentrated sugar solution containing Arabic gum, talcum, polyvinylpyrrolidone, carbopol gel, polyethylene glycol, titanium oxide, cellulose nitrate, and proper organic solvent or solvent combination. Different combinations of coloring matter or edible pigment can be added to the tablets or coat of sugar-coated tablets to discriminate or designate the active compound.

The drug combination for oral administration includes the stuffing-type capsule and the sealed soft capsule made of glutin and a plasticizer such as glycerin or sorbic acid. The stuffing-type capsule contains a filler, such as lactose, an adhesive, such as starch, and/or a lubricant, such as talcum or stearate. In addition, a stabilizer can also be used to stabilize the active components. In the soft capsule, the active compound can be dissolved or suspended in some proper liquid, such as fatty oil, liquid olefin, or liquid-like polyethylene glycol. Besides, a stabilizer can also be added. All the dosage formulations for oral administration should be convenient for patients. In the case of actinal administration, the above mentioned combination can be prepared into the convenient dosage formulations of troche.

In the case of inhalation administration, the pharmaceutical compositions capable of treating a disease associated with immunosuppression can be readily released in the form of aerosol by use of high-pressure package or atomizer, or by use of some proper propellant such as dichlorodifluoromethane, trichlorofluoromethane, dichlorotetrafluoroethane, carbon dioxide or other proper gases. In the case of high-pressure aerosol, the dosage unit can be defined by the quantity of measured release with one valve. The glutin capsule and cartridge used as insufflator or exsufflator can be produced as a mixture containing the peptides and a proper pulverous substrate (such as lactose or starch).

The pharmaceutical compositions capable of treating a disease associated with immunosuppression can be prepared into a dosage formulation for extragastrointestinal administration. For example, they can be prepared into a formulation for injections that include cluster-drug injection or continuous intravenous infusion. The preparation for injection use can be packed in the form of unit dosage. For example, it can be packed into ampoules. Preparations in large dosage can also be packed in the form of unit dosage, such as ampoule or large-dosage container, and added with preservative. The combinations of the present invention can take the form of suspension, solution or emulsion with oil or water as its medium, and can contain some additives, such as a suspending agent, stabilizer, and/or dispersant.

The drug combinations for extragastrointestinal administration can be in a water solution of the active substance, namely the water-dissolved form. The suspension of the active substance can also be produced as a proper oil-like suspension injection. The proper oleophilic solvent or vector includes fatty oil such as gingeli oil, or synthesized fatty acid ester such as ethyl oleate or triglyceride, or liposome. Water-like suspension for injection can contain substance that increases the suspension viscosity, such as sodium carboxymethyl cellulose, sorbic alcohol, and glucosan. The above mentioned suspension can also contain selectively a proper stabilizer or substance that increases the compound solubility in order to prepare a high-concentration solution. The active component of the pulverous injection can be dissolved in some proper solvent, such as sterile water for injection that is in the absence of pyretogen, before administration.

The pharmaceutical compositions capable of treating a disease associated with immunosuppression can also be prepared into rectal dosage formulations such as suppositories or retained enemas. They can be prepared with frequent substrate such as cacao butter or other glyceryl esters.

Apart from the dosage formulations that have been described, the pharmaceutical compositions capable of treating a disease associated with immunosuppression can also be prepared as long-acting dosage formulations that can be administered by hypodermal or intramuscular planting or intramuscular injection. Therefore, the peptides and its derivatives or drug combinations can be prepared with proper polymers, hydrophobes (oil emulsion, for example), ion exchange chromatography, or hardly soluble derivatives, such as hardly soluble salt.

The drug carriers for hydrophobic peptides or combinations of the present invention are a co-dissolved system of organic polymers and aqueous phase that blends with water and contains benzyl alcohol and non-polar surfactant. This co-dissolved system can be a VPD co-dissolved system. VPD is a solution containing 3% (W/V) benzyl alcohol, 8% (W/V) non-polar surfactant multiethoxyaether and 65% (W/V) polyethylene glycol 300 in absolute alcohol, while a VPD co-dissolved system (VPD: 5W) is prepared with VPD diluted in water by 1:1 and 5% glucose. This kind of co-dissolved system can dissolve hydrophobes better while it will produce low toxicity in systemic administration. As long as its solubility and toxicity are not changed, the proportions of the co-dissolved system can be altered greatly. In addition, the components of the co-dissolved carrier can also be changed. For example, other non-polar surfactant with low toxicity can be used to substitute for multi-ethoxyaether; the proportion of polyethylene glycol can also be changed; other biologically-blending polymers, such as polyvinylpyrrolidone, can be used to substitute for polyethylene; other sugar or polyose can be used to substitute for glucose.

The drug combinations can also include proper carrier-like excipients in solid or gel phase. These carriers or excipients include (but not limited to) calcium carbonate, calcium phosphate, various sugar, starch, cellulose derivatives, gelatin, or polymers, such as polyethylene glycol. The drug combinations of the present invention also include the combination of active components in effective dose used to obtain the therapeutic purpose. The method of determining effective dose is well-known to one of skill in the art.

In another embodiment, the pharmaceutical composition can be delivered in a vesicle, in particular a liposome (see, e.g., Langer (1990) Science 249:1527-1533).

In yet another embodiment, the pharmaceutical composition can be delivered in a controlled release system. In one embodiment, a pump may be used (Buchwald (1980) Surgery 88:507; Saudek et al. (1989) N. Engl. J. Med. 321:574). In another embodiment, polymeric materials can be used (see Medical Applications of Controlled Release (1974) Langer and Wise (eds.), CRC Pres., Boca Raton, Fla.; Controlled Drug Bioavailability, Drug Product Design and Performance, Smolen and Ball (eds.), Wiley, New York (1984); Ranger and Peppas (1983) J. Macromol. Sci. Rev. Macromol. Chem. 23:61; Levy et al. (1985) Science 228:190; During et al. (1989) Ann. Neurol. 25:351; Howard et al. (1989) J. Neurosurg. 71:105). In yet another embodiment, a controlled release system can be placed in proximity of the composition's target, i.e., the breast tissue, thus requiring only a fraction of the systemic dose (see, e.g., Goodson, in Medical Applications of Controlled Release, vol. 2, pp. 115-138 (1984). Other controlled release systems are discussed in the review by Langer (1990, Science 249:1527-1533).

The pharmaceutical compositions capable of treating a disease associated with immunosuppression may further comprise a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences (2005) 21st Edition, Wiley. The formulation should suit the mode of administration.

In a preferred embodiment of the present invention, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions capable of treating a disease associated with immunosuppression can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition capable of treating a disease associated with immunosuppression which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems. Suppositories generally contain active ingredient in the range of 0.5% to 10% by weight; oral formulations preferably contain 10% to 95% active ingredient.

Another aspect of the invention is directed toward use of the biosensors of the present invention as part of a kit used to detect the modulations in tryptophan concentration, and tryptophan/kynurenine exchange. Kits of the invention include one or more containers comprising by way of example, and not limitation, nucleic acids encoding LAT-1, LAT-2, or IDO, or combinations thereof, a LAT-1, LAT-2, or IDO recombinant protein or combinations thereof and instructions for use in accordance with any of the methods of the invention described herein. The biosensors of the invention may be used in a variety of assays for tryptophan concentration determination and for monitoring tryptophanikynurenine exchange. The containers may be unit doses, bulk packages (e.g., multi-dose packages) or sub-unit doses. The kits of this invention are in suitable packaging. Also contemplated are packages for use in combination with a specific device, such as an inhaler, nasal administration device or an infusion device. A kit may have a sterile access port. The container may also have a sterile access port. Kits may optionally provide additional components such as buffers and interpretive information.

Without further description, it is believed that one of ordinary skill in the art can, using the preceding description and the following illustrative examples, make and utilize the agents of the present invention and practice the claimed methods. The following working examples are provided to facilitate the practice of the present invention, and are not to be construed as limiting in any way the remainder of the disclosure.

EXAMPLES

Materials and Methods

Chemicals, strains, plasmids. All chemicals were of analytical grade and purchased from Sigma-Aldrich. *E. coli* strains DH5α, TOP10 F' and BL21(DE3)gold (Stratagene) were used for transformation of Gateway reactions, cloning, and protein production, respectively.

Construction of FLIPW and FLIPpur sensors. The *E. coli* trpR gene (Gunsalus and Yanofsky, (1980) (EcoGene EG11029, TrpR: UniProt P0A881) was amplified from genomic DNA by PCR for cloning in plasmid pGWF1 through pDONR using forward primer (5'-GGGGA-CAAGTTTGTACAAAAAAGCAGGCTCGGC-CCAACAATCAC CCTATTCAGC-3') (SEQ ID NO: 2) and reverse primer (5'-GGGGACCACTTTGTAC AAGAAAGCTGGGTT ATCGCTTTTCAGCAACAC-CTCTTC-3') (SEQ ID NO: 3) using the Gateway protocol provided by the manufacturer (Invitrogen). Plasmid pGWF1 is based on the pRSETb expression vector (Novagen) and contains genes for enhanced cyan fluorescent protein (eCFP) and Venus, a yellow fluorescent protein variant, cloned under control of the bacteriophage T7 promoter. Between the gene sequences of eCFP and Venus a chloramphenicol-resistance gene and lethal ccdB gene are flanked by attP DNA sequences for insertion of DNA sequences using Gateway cloning technology. The trpR gene was sandwiched between the eCFP and Venus coding sequences resulting in plasmid pTK164. The protein sequence encoded on pTK164 was denoted FLIPW-CTY. By PCR, trpR copies flanked with BamHI or HindIII restriction site sequences were produced. Twin cassette sensor variants were constructed by insertion of trpR copies into pTK164 using unique BamHI and HindIII restriction sites respectively before the ECFP coding sequence (resulting in pTK203) and after the Venus encoding sequence (resulting in pTK204), resulting in sensor variants encoding the repressor dimer in a single gene. A construct in which two trpR copies were connected with a Gly$_7$ linker was denoted pTK205. The gene products of pTK203, pTK204, and pTK205 were denoted FLIPW-TCTY, FLIPW-CTYT, and FLIPW-CTTY, respectively. The part of the *E. coli* purR gene (EcoGene EG10800, PurR: Uniprot P0ACP7) encoding amino acid residues 56 to 341 was amplified from genomic DNA by PCR using forward primer (5'-GGTACCGGAGGCGG CGT-TAACCACACCAAGTCTATCG-3') (SEQ ID NO: 4) and reverse primer (5'-GGTACCGG CGCCTTTACGACGAT-AGTCGCGGAACGG-3') (SEQ ID NO: 5) and cloned into pCR4TopoBlunt (Invitrogen). DNA sequencing revealed two T→C mutations at positions 534 and 788, resulting in substitution Leu263Pro (unmodified PurR numbering). Previously-described affinity mutation Arg190Gln (Lu et al., 1998) was introduced by PCR using primers (5'-GAAATCGGC GTCATCCCCGGCCCGCTGGAACA GAACACCGGCG-CAG-3') (SEQ ID NO: 6) and (5'-CTGCGCCGGTGTTCT-GTTCCAGCGGGCC GGGGATGACGCCGATTTC-3') (SEQ ID NO: 7). PurR_R190Q was excised from pCR$_4$TopoBluntPurR_R190Q by KpnI and cloned into KpnI-digested pRSET_Flip derived from FLIPrib-250n (Lager et al., 2003), resulting in pFLIPpur encoding a His$_6$-eCFP-PurR-cYFP fusion protein. FLIPW and FLIPpur constructs were harbored in *E. coli* BL21(DE3)gold and sensor proteins were produced and purified as described previously (Fehr et al., 2002).

In vitro characterization of FLIPW and FLIPpur sensors. Purified sensor was added to a dilution series of ligand in 20 mM MOPS pH 7.0 (FLIPW) or 20 mM MES pH7.0 (FLIP-pur) in the range of $10^{-2}$ to $10^{-6}$ M and analyzed in a monochromator microplate reader (Satire, Tecan, Austria; eCFP excitation 433/12 nm, eCFP emission 485/12 and Venus emission 528/12 nm). eCFP shows two emission peaks at 476 nm and 501 nm (LaMorte et al., 2003). The eCFP emission used for the ratio calculation was determined at 485 nm. Protein was diluted to give Venus/eYFP readouts of 20,000 to 30,000 at a manual gain between 70-75. By using the change in FRET ratio upon binding of ligand, affinity constants ($K_d$) were determined by fitting the titration curves to a single-site-binding isotherm: $R=R_{apo}+(R_{sat}-R_{apo})\cdot(n\cdot[L])/(K_d+[L])$ with [L], ligand concentration; n, number of equal binding sites; R, ratio; $R_{apo}$, ratio in the absence of ligand; and $R_{sat}$, ratio at saturation with ligand. Three independent protein preparations were analyzed and each protein preparation was analyzed in triplicate.

3D modeling of FLIPTrpR variants. Structural models of FLIPW sensors were constructed using the crystal structures of Trp repressor in complex with L-Trp (PDB identifier 1WRP) and Venus (1MYW). Proteins were manually docked in the various topologies using MAGE (kinemage.biochem.duke.edu).

Tissue culture and transfection. For cytosolic expression in COS-7 cells, the gene encoding CTYT was amplified by PCR with primers encoding unique BamHI and EcoRI restriction sites at the 5' and 3' end, respectively, and cloned into BamHI/EcoRI digested peDNA3.1(+) vector (Invitrogen), resulting in plasmid pTK222. COS-7 cells were grown in Dulbecco's modified Eagle's medium (high glucose; DMEM, Gibco) with 10% fetal calf serum and 50 µg; ml penicillin and 50 µg/ml streptomycin (Gibco). Cells were cultured at 37° C. and 5% CO2. For imaging, cells were cultured in 8-well LabTekII German tissue culture glass slides (Nalg Nunc International) and transiently transfected at 50-70% confluence using Lipofectamine 2000 Reagent (Invitrogen) in Opti-MEM I reduced serum medium (Gibco): After transfection, cells were cultured for 16 hours in Opti-MEM followed by 3 hours in DMEM prior to imaging. Transfection efficiency as determined by counting fluorescing cells was at least 30%.

Microplate assays. Adherent cells in 96-well microplates were washed once with 100 µl Tyrode's buffer (119 mM NaCl, 2.5 mM KCl, 2 mM CaCl$_2$, 2 mM MgCl$_2$, 25 mM HEPES, 30 mM glucose, pH 7.3-7.4). The initial FRET ratio was measured by recording the eCFP and Venus emissions at 485 nm and 528 nm, respectively, after excitation of eCFP at 433 nm in a Safire monochromator microplate reader (Tecan, Grodig, Austria). Standard deviation of the initial ratios was less than 10%. After addition of 100 µl tryptophan in Tyrode's buffer the FRET ratio was recorded with 2 min intervals for up to two hours. Uptake rates were determined from linear parts in the initial FRET change and fitted with the non-linear regression program Origin 6.1 (OriginLab, Northhampton, Me., USA).

Imaging. Ratio imaging was performed on an inverted fluorescence microscope (DM IRE2, Leica) with a Quant EM digital camera (Photometrics) and 20× oil immersion, 63× water immersion lenses (HC PL APO 20×/0.7 or HCX PL APO, Leica, Germany). Dual emission intensity ratios were simultaneously recorded using a DualView with an OI-5-EM filter set (eCFP 480/30; eYFP 535/40; Optical 17 Insights, USA) and Metafluor 6.3r6 software (Molecular Devices, USA). A Sutter Instruments Lambda DG4 provided excitation. Images were acquired within the linear detection range of the camera and exposure times varied between 50 to 200 ms, depending on the expression level, with software binning between 2 and 3. Fluorescence intensities for eCFP and Venus were typically in the range of 6000-8000 and 12000-16000, respectively. Typical background values were around 1000. Cells were perfused with Tyrode's buffer at flow rates of 1.0 ml/min in a vacuum chamber with a total volume of 0.1 ml. Inhibitors BCH and MeIAB were used at 5 mM concentrations. For determination of the substrate specificity of the tryptophan exchange, all 20 amino acids were tested at 100 µM concentrations. Analyses were repeated at least three times with similar results.

Example 1

A Ligand-Binding Scaffold for L-Tryptophan

Figure 1B:
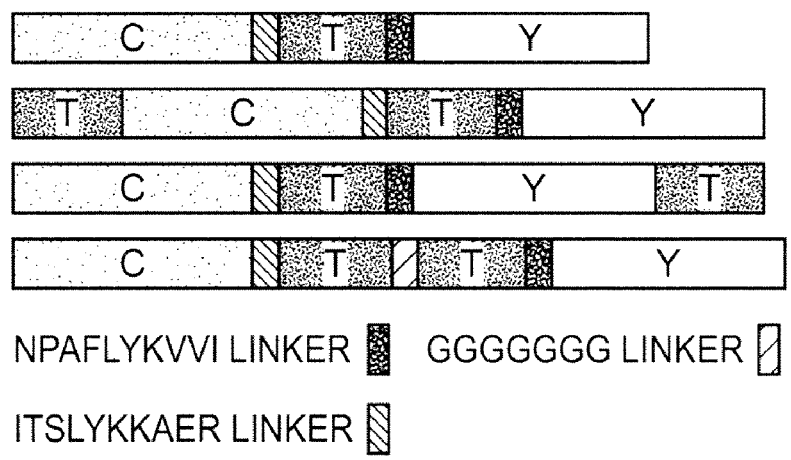
Figure 1C:
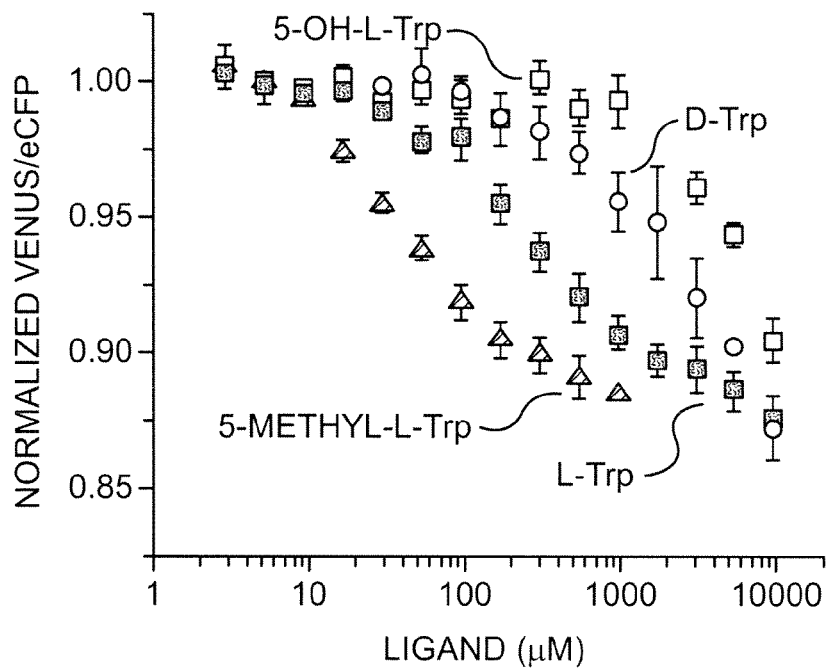

The *E. coli* tryptophan operon repressor TrpR is an all-helical polypeptide of 108 amino acids organized into 6 α-helices. This polypeptide forms a dimer that selectively binds two molecules of L-tryptophan with micromolar affinity (FIG. 1A) (Marmorstein et al., 1987). In the active, dimeric conformation of TrpR, 5 of the 6 helices in each polypeptide are involved in intermolecular contacts (Schevitz et al., 1985). With both chains contributing to each tryptophan-binding site, two TrpR polypeptides are necessary to form two functional intermolecular binding sites (FIG. 1A). In the absence of tryptophan, a part of TrpR is unfolded (Reedstrom and Royer, 1995), which likely corresponds to the helix-turn-helix motifs that form the 'DNA-reading heads.' Crystallographic analysis shows that the helix-turn-helix motif undergoes structural rearrangements upon binding of tryptophan (Zhang et al., 1987), and the motif's flexibility is essential for the recognition of operator sequences (Gryk et al., 1996). In addition, tryptophan binding results in a shift of the relative distance and orientation of the N- and C-termini of each repressor polypeptide with respect to one another (Zhang et al., 1987), which was detected as a change in fluorescence resonance energy transfer (FRET) when TrpR was fused to a FRET fluorophore pair. The *E. coli* tryptophan repressor gene was sandwiched between eCFP and Venus coding sequences (FIG. 1B). Production of the translated fusion product FLIPW-CTY (CTY=eCFP-TrpR-VenusYFP) in *E. coli* was readily detected by recording the emission spectrum of the eCFP-Venus FRET signal in whole cell cultures. When eCFP was excited, significant energy transfer to Venus was detected, resulting in a Venus/'eCFP ratio of 4 (see Table 1). Addition of L-tryptophan decreased FRET efficiency of the purified protein, visible as an increase in eCFP emission intensity and a concomitant decrease in Venus fluorescence intensity, resulting in a 10% reduction in the Venus/eCFP ratio (FIG. 1C). FLIPW-CTY bound L-tryptophan with an apparent $K_d$ of 220±20 µM, which is about an order of magnitude larger than unmodified TrpR as measured by equilibrium dialysis (Marmorstein et al., 1987). Small molecules are known to efficiently quench fluorophore emission due to nonspecific interactions (Lakowicz, 1999). To exclude that the negative ratio change observed for FLIP-CTY is due to unspecific effects, the FRET response was measured in the presence of D-tryptophan. Compared to L-tryptophan, unmodified TrpR has a 20-fold reduced affinity for D-tryptophan (Marmorstein et al., 1987). Titration of FLIPW-CTY with D-tryptophan resulted in a decrease of FRET ratio at about 5-fold higher concentrations than L-tryptophan. Since D- and L-tryptophan would be expected to have the same quenching properties, this strongly suggested that the decrease in FRET ratio of FLIPW-CTY is due to a specific interaction of the sensor with tryptophan (FIG. 1C). Analogous to the wild-type TrpR, FLIPW-CTY binds ligands in order of decreasing affinity: L-5-methyl-tryptophan>L-tryptophan>D-tryptophan>L-5-hydroxy-tryptophan (see Table 2) (Marmorstein et al., 1987).

TABLE 1

Signal change and L-tryptophan affinities of FLIPW sensors

| Sensor | Apo ratio* | Δratio | Δratio (%) | $K_d$ (µM) |
|---|---|---|---|---|
| FLIPW-CTY | 4.10 | −0.41 | −10 | 220 ± 20 |
| FLIPW-TCTY | 1.57 | −0.03 | −2 | 20 |
| FLIPW-CTYT | 2.08 | 0.35 | 17 | 210 ± 20 |
| FLIPW-CTTY | 2.85 | n.d.[†] | n.d.[†] | n.d.[†] |

*ratio defined as fluorescence intensity quotient of emission at 528 nm/485 nm
[†]n.d. not determined

TABLE 2

Affinities of FLIPW-CTY and FLIPW-CTYT for tryptophan substrates (mM).

| Substrate | FLIPW-CTY | FLIPW-CTYT |
|---|---|---|
| L-tryptophan | 0.22 ± 0.02 | 0.21 ± 0.02 |
| D-tryptophan | 3.1 ± 0.3 | n.d.* |
| L-5-methyl-tryptophan | 0.06 ± 0.01 | 0.06 ± 0.02 |
| L-5-hydroxy-tryptophan | 6.0 ± 0.8 | n.d.* |

*n.d. not determined

Example 2

Twin-Cassette FLIPW Nanosensor Variants

Figure 1D:
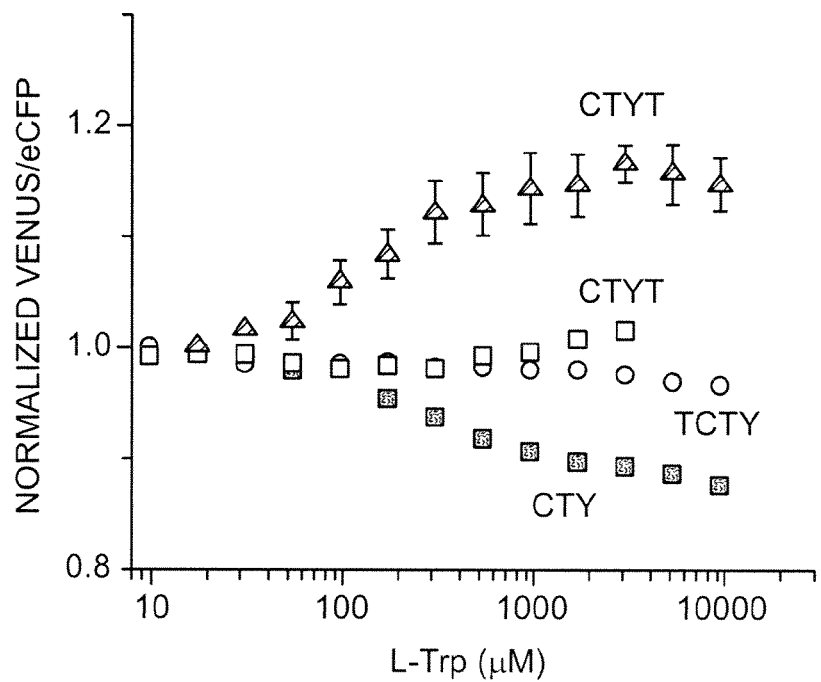
Figure 7:
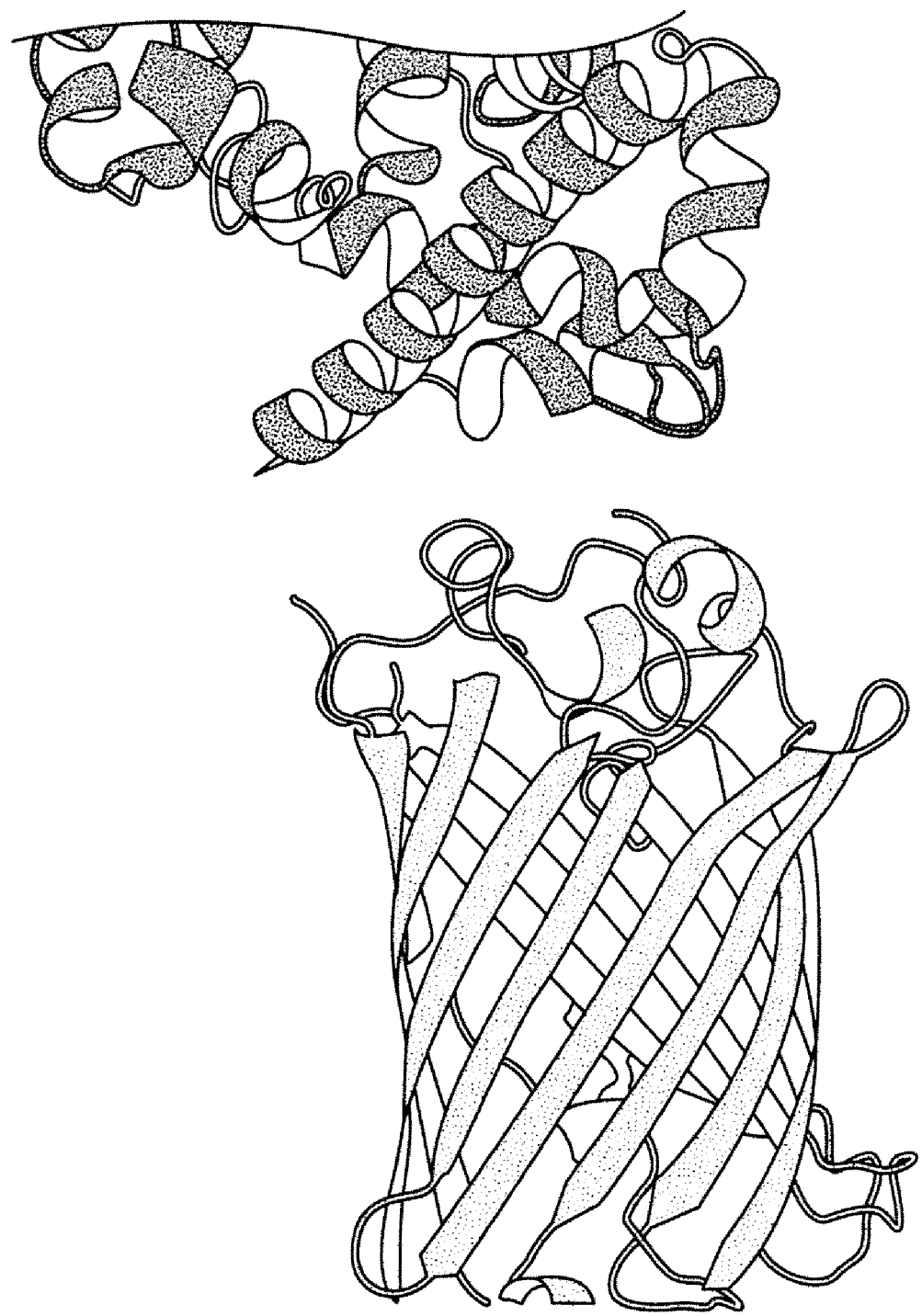
FIG. 7 shows the relative position of the components of the FLIPW-CTYT sensor. The TrpR dimer (PDB: 1WRP) and Venus (PDB: 1MYW) are modeled to be sterically compatible, with the termini approaching within 1 Å.

The active conformation of TrpR is a dimer and two tryptophan binding sites are formed at the dimer interface (Otwinowski et al., 1988). Therefore, one assumes that the functional FLIPW-CTY sensor is a dimer of two CTY polypeptides with the four fluorophores being packed tightly together, potentially affecting the binding affinity due to steric hindrance or resulting in signal loss due to averaging of the fluorophore signals. Thus, fusing two TrpR molecules to one fluorophore set likely gives rise to sensors with a single eCFP-Venus pair per sensor, which may have improved sensing characteristics. Three sensor permutations containing two TrpR copies (a and b) in a single gene product were constructed (FIG. 1B). In the pet niutants FLIPW-TCTY (linear arrangement of TrpR[a]-eCFP-TrpR[b]-Venus) and FLIPW-CTYT (linear arrangement of eCFP-TrpR[a]-Venus-TrpR[b]) the distance between the N- and C-terminus of the intercalated green fluorescent protein variants (eCFP in TCTY and Venus in CTYT) corresponds well to the distance between the C-terminus of the first TrpR polypeptide (a) and the N-terminus of the second TrpR (b) in the dimer (~22 Å, see FIG. 7). One of the fluorophores in these variants is therefore rotationally constrained by these attachment points, which is expected to lead to an improvement of the signal change due to decreased conformational averaging as shown for other 'insertional' FRET sensors (Deuschle et al., 2005; Van der Meer et al., 1994). The third variant FLIPW-CTTY is a linear fusion in the order eCFP-TrpR[a]-TrpR[b]-Venus. For the construction of FLIPW-CTTY, two copies of the repressor gene were connected by a flexible linker consisting of 7 glycine residues and inserted between the fluorophores. This linker was designed to loosely connect the two TrpR proteins without changing the dimer conformation, and is based on a model constructed in Modeller8v1 (Marti-Renom et al., 2000). While the FRET ratio of FLIPW-CTTY and FLIPW-TCTY changed only slightly when titrated with L-tryptophan, FLIPW-CTYT yielded a significantly improved tryptophan sensor (FIG. 1d). The apparent binding constant of FLIPW-TCTY for L-tryptophan was around 20 µM, comparable to unmodified TrpR (Marmorstein et al., 1987). The ratio change observed for FLIPW-CTTY could not be fitted with a formula for a single-site-binding isotherm (see Material and Methods).

When FLIPW-CTYT was titrated with L-tryptophan an increase in FRET ratio from 2.0 to 2.35 was observed, indicating a significant change in chromophore orientation with respect to FLIPW-CTY. The ratio change observed in vitro for FLIPW-CTYT was +17%. FLIPW-CTYT bound L-tryptophan with an apparent affinity of 210±20 µM. The positive ratio change permits efficient discrimination of quenching effects, thus FLIPW-CTYT appears better suited for in vivo measurements compared to FLIPW-CTY, which shows a negative ratio change (see Table 1). Therefore FLIPW-CTYT was chosen to monitor physiological tryptophan levels in mammalian cells (dynamic range ~25 µM to 2 mM).

Example 3

Molecular Modeling of FLIPW Sensors

Figure 2A:
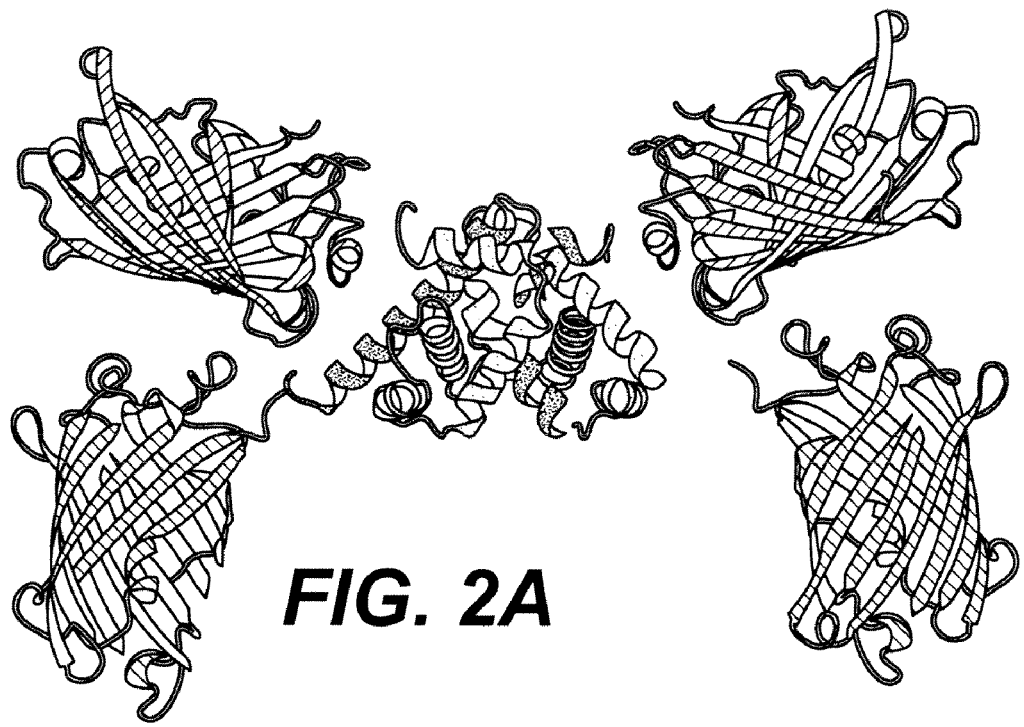
FIGS. 2A-B show the structural models of FLIPW-CTY and FLIPW-CTYT tryptophan sensors. TrpR: (PDB: 1WRP), eCFP (based on PDB: 1MYW) and Venus (PDB: 1MYW).
Figure 2B:
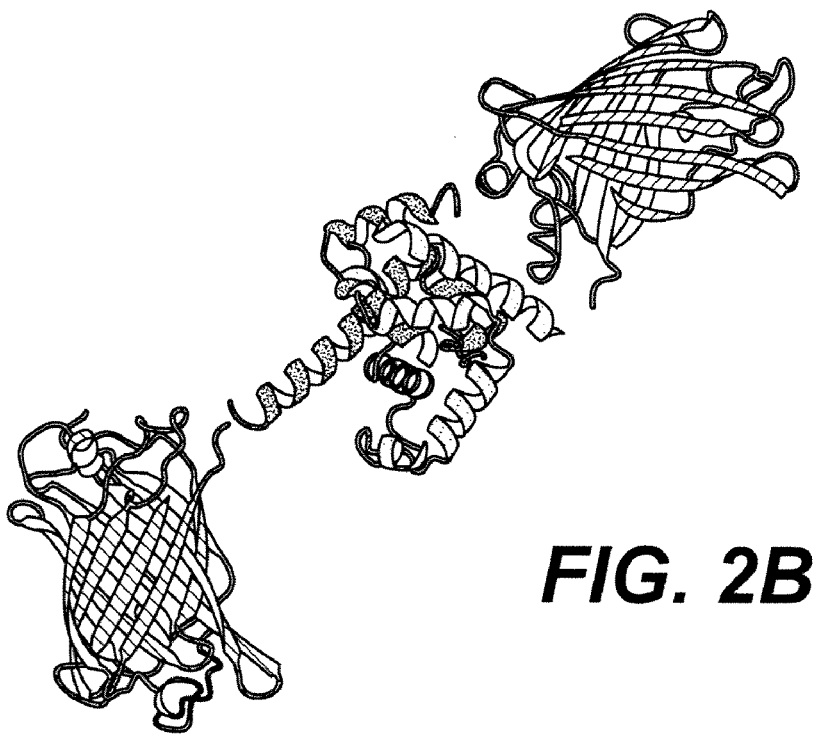
Figure 8A:
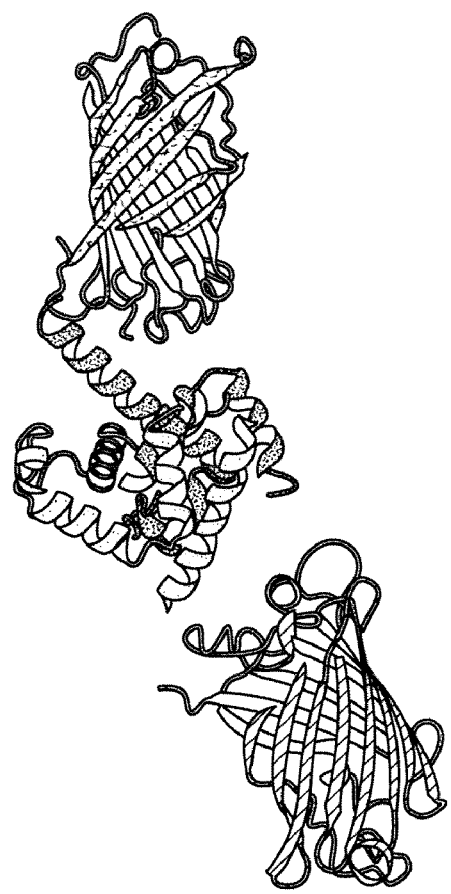
FIG. 8A shows the FLIPW-TCTY monomer.
Figure 8B:
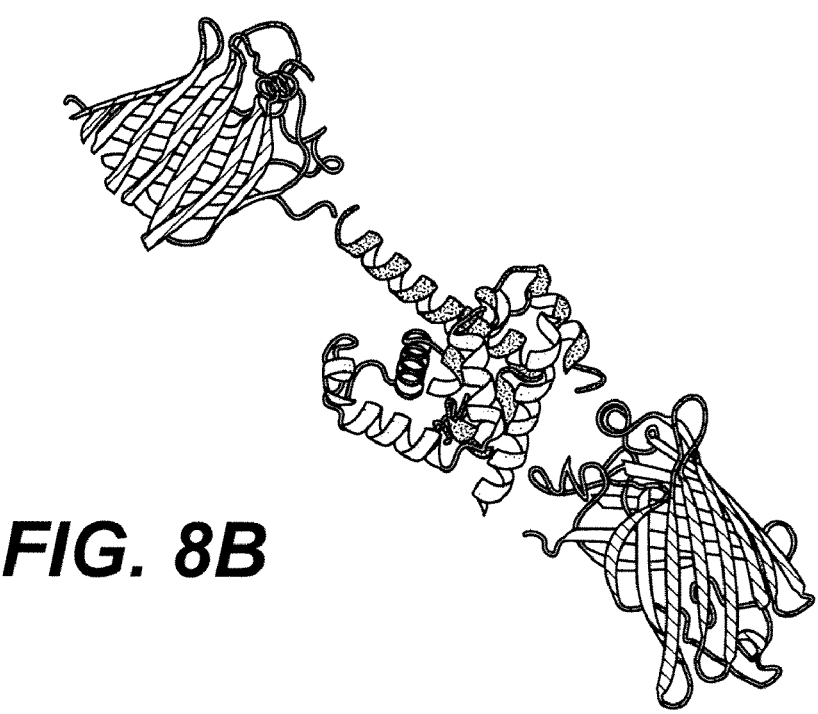
FIG. 8B shows the FLIPW-CTYT monomer.

Molecular modeling was performed to rationalize the observed FRET signal changes. The original sensor, FLIPW-CTY, is predicted to dimerize, resulting in an antiparallel arrangement of the TrpR polypeptides, thus resulting in two sets of eCFP and Venus fluorophores in close vicinity at both sides of the TrpR dimer (FIG. 2A). In agreement with the close vicinity of the fluorophores, FLIPW-CTY showed the highest FRET efficiency. The FLIPW-CTYT sensor is modeled to form a functional TrpR dimer intra-molecularly, resulting in a single eCFP and a single Venus molecule per sensor (FIG. 2B). FLIPW-CTYT has lower absolute energy transfer efficiency, consistent with the greater distance between the fluorophore dipoles. The relative FRET change is higher compared to FLIPW-CTY, probably due to the rigidification of the Venus molecule by its fusion to both TrpR monomers. The FLIPW-CTTY and FLIPW-TCTY sensors do not show sufficient ligand-dependent ratio changes to be useful as sensors. Molecular modeling explains the different response of the FLIPW-CTYT and FLIPW-TCTY sensors. In FLIPW-CTYT, a fluorophore is attached to the N-terminus of TrpR$^a$, leading to a different spatial arrangement and rotational probability space compared to FLIPW-TCTY, in which Venus is attached to the C-terminus of TrpR$^b$. This geometrical difference is presumably transduced into altered dipole orientations in the FLIPW-CTYT sensor (FIG. 8).

Example 4

Tryptophan Uptake in COS-7 Cell Cultures in 96-Well Microplates

Figure 3A:
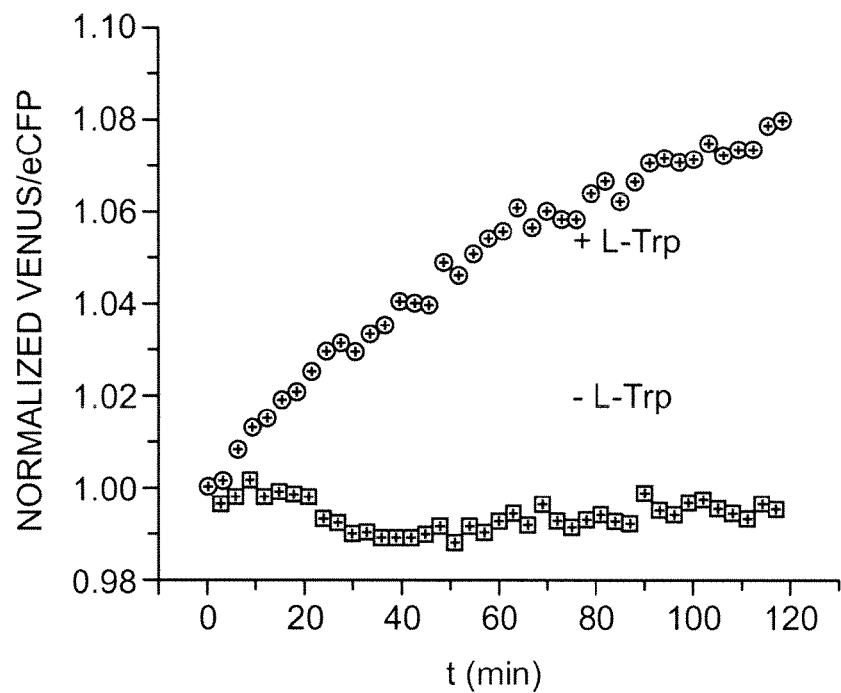
FIGS. 3A-B show the uptake of tryptophan by COS-7 cell cultures in 96-well microplates monitored with FLIPW-CTYT.
Figure 3B:
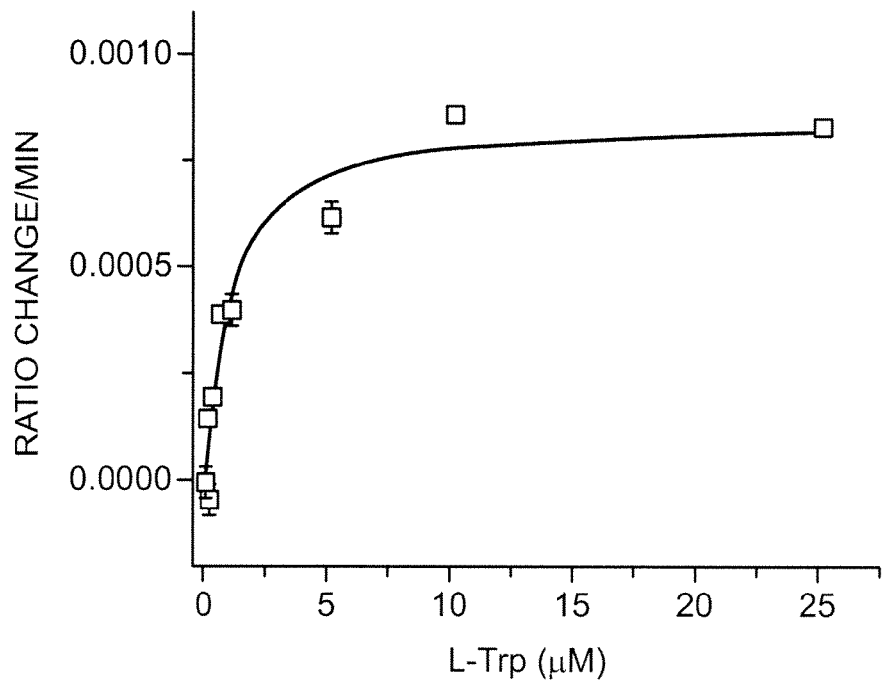

To measure tryptophan flux in the cytosol of live cells, COS-7 cell cultures seeded in a 96-well microplate were transiently transfected with pTK222 for cytosolic production of FLIPW-CTYT sensor. Microscopic analysis of transfected cells showed that FLIPW-CTYT was produced exclusively in the cytosol and did not enter the nucleus, similar to results obtained with the glucose FRET sensor in COS-7 cells (Fehr et al., 2003). When microwell-grown cells expressing FLIPW-CTYT were incubated in Tyrode's buffer containing tryptophan and analyzed in a microplate reader, an increase in FRET ratio was observed indicating an increase in cytosolic tryptophan levels as a result of uptake (FIG. 3A). The rate in FRET increase depended on the external tryptophan concentration and showed Michaelis-Menten type kinetics with an apparent enzymatic specificity constant $K_M$ of 0.88±0.27 µM for combined transport and metabolism (FIG. 3B). The FLIPW-CTYT sensor is thus suitable to study factors influencing tryptophan transport and metabolism and can be used in high-throughput fluorescence-based assay systems.

Example 5

Tryptophan Uptake and Exchange in COS-7 Cells is Mediated by LAT1

Figure 4A:
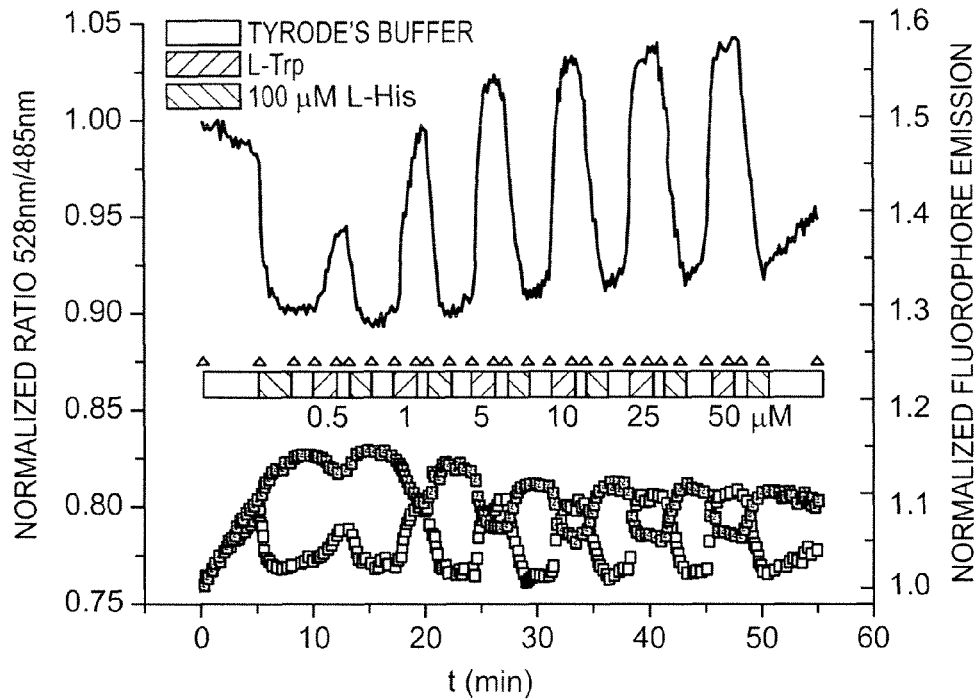
FIGS. 4A-C show the imaging of intracellular tryptophan levels with FLIPW-CTYT in COS-7 cells.
Figure 4B:
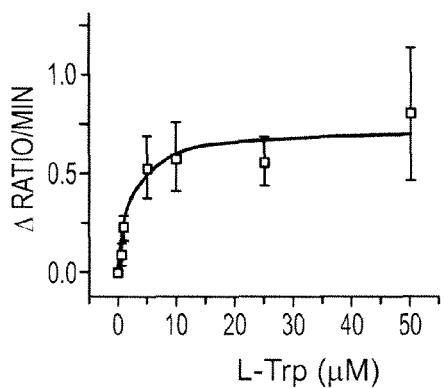
Figure 4C:
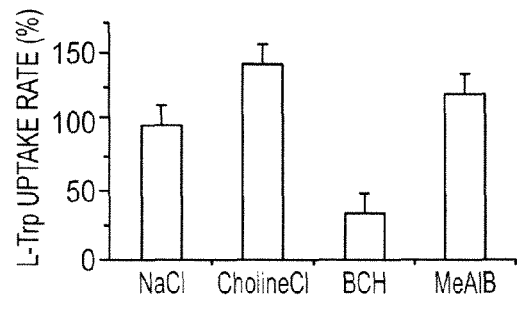

Cytosolic tryptophan levels in mammalian cells have been estimated at ~250 µM, which is compatible with the detection range of the FLIPW-CTYT sensor. When COS-7 cells producing cytosolic FLIPW-CTYT sensor were perfused with Tyrode's buffer, the initial FRET ratio (Venus-to-eCFP signal) was stable (FIG. 4A). Upon perfusion with 100 µM L-tryptophan, the FRET ratio immediately increased, corresponding to rising levels of cytosolic tryptophan. The FRET ratio was stable during subsequent perfusion with buffer, indicating that the cytosolic steady-state tryptophan levels are stable and that in COS-7 cells tryptophan permeases like TAT1 (Kim et al., 2002) do not contribute significantly. When L-histidine was provided in the medium, the ECFP emission increased and VENUS emission decreased, evidencing a decrease in FRET efficiency as a result of export of tryptophan from the cytosol. This way, cells could be repeatedly loaded with tryptophan and unloaded using histidine (FIG. 4A). By comparison of the starting, minimum, and maximum response levels of the sensor, assuming that the $K_D$ of the sensor expressed in cells was the same as during the in vitro characterization, the cytosolic tryptophan concentration was estimated at 340 µM. The affinity of the cells for combined uptake and metabolism of tryptophan was 2.6±1.1 µM (FIG. 4B). The system L inhibitor 2-aminobicyclo-(2,2,1)-heptane-2-carboxylic acid (BCH) decreased the uptake of tryptophan, while either replacement of sodium with choline or the transport system A inhibitor γ-(methylamino)isobutyric acid did not decrease uptake rates (FIG. 4C). NC-independence and BCH sensitivity are consistent with the transport properties of LAT1 and LAT2 amino acid counterexchangers (Verrey, 2003). Like histidine, the larger hydrophobic and aromatic amino acids leucine, isoleucine, valine, methionine, phenylalanine, and tyrosine were able to promote tryptophan export (at 100 µM concentrations, data not shown), which corresponds best to the reported substrate specificity of LAT1 (Kanai et al., 1998; Pineda et al., 1999; Yanagida et al., 2001). LAT2 is expressed in the proximal tubule of the kidney (Verrey, 2003), so it might be expressed in COS-7 cells. In addition, LAT1 is expressed in various human tumor cell lines (Yanagida et al., 2001) and, consequently, is likely to be present in COS-7 cells as well.

Example 6

Tryptophan is Exchanged for its Kynurenine Degradation Products

Figure 5B:
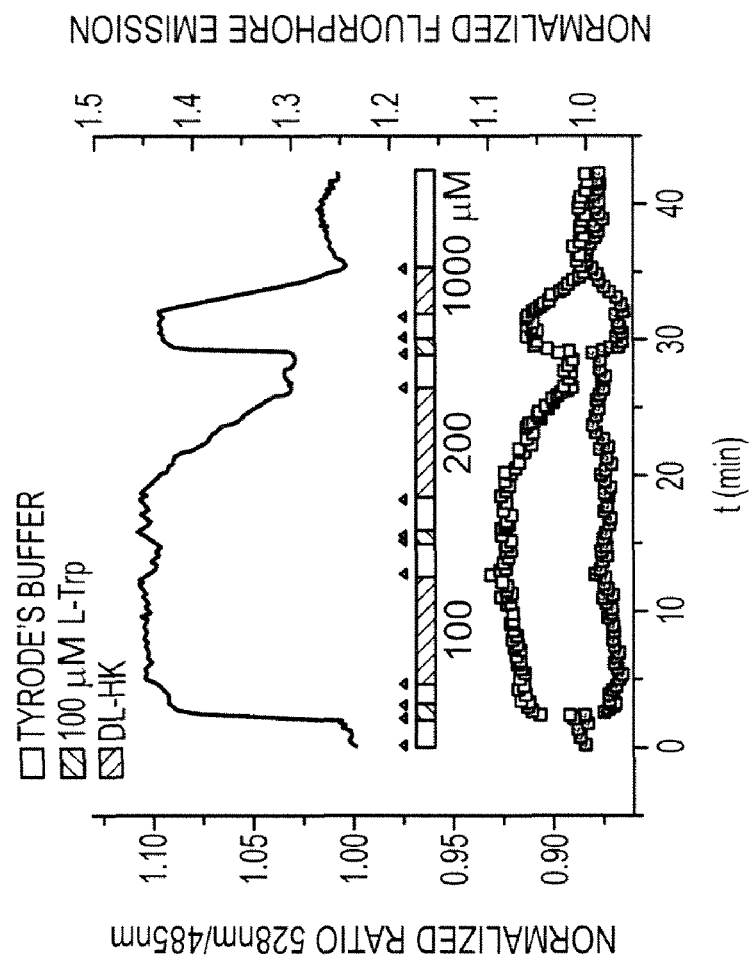
FIGS. 5A-B show the imaging of tryptophan-kynurenine exchange with FLIPW-CTYT in COS-7 cells.
Figure 5A:
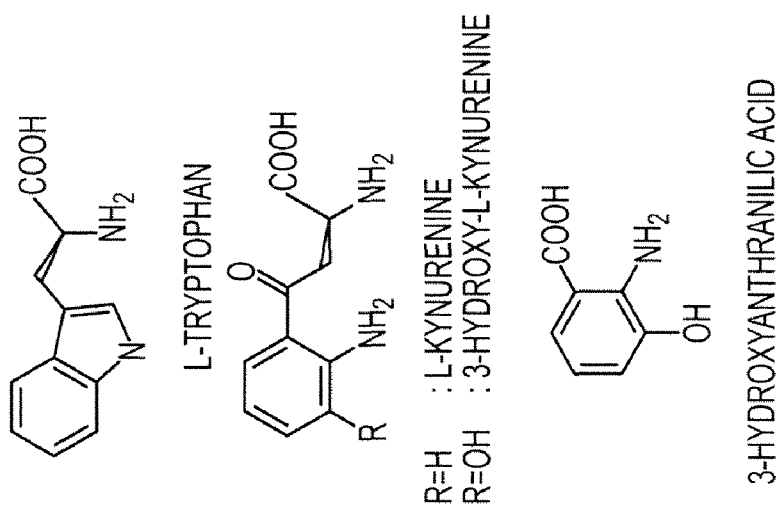

The product of tryptophan conversion by IDO is formylkynurenine (FK), which is in turn converted by the enzyme kynurenine formamidase to kynurenine (K) (FIG. 5A). The consecutive action of kynurenine-3-hydroxylase produces 3-hydroxy-kynurenine (HK), which is further degraded by kynureninase to hydroxy-anthranilic acid (HAA) (FIG. 5A). In vitro, K, HK, and HAA did not result in a FLIPW-CTYT response or interfere with tryptophan binding to the sensor (data not shown). The effect of extracellular K, HK and HAA on the intracellular tryptophan levels in preloaded COS-7 cells was tested next. Both extracellular K and HK resulted in reduction of the fluorophore emission ratios in the COS-7 cells, evidencing tryptophan export. The sensor responses for the K- and HK-induced tryptophan were similar (data not shown) and HK-induced export is shown in FIG. 5B. Extracellular HAA did not result in tryptophan export (data not shown). Thus, the LAT transporters that are present in COS-7 cells exchange tryptophan for its degradation products K and HK. As tryptophan, K and HK are all substrates for LAT1, one may speculate that also FK may be as well. Since the substrate specificities of LAT1 and LAT2 differ in the transport of small amino acids amino acids (Meier et al., 2002; Pineda et al., 1999), it is assumed that they are both capable of tryptophan-kynurenine exchange.

Example 7

Using FRET to Monitor Metabolism of Tryptophan

It was also assessed whether affecting the metabolism of tryptophan could be monitored using the FRET nanosensors. The induction of indoleamine 2,3-dioxygenase (IDO) by interferon-gamma in KB cells has been described by Ozaki et al. (Proc. Natl. Acad. Sci. U.S.A. (1988)85: 1242-1246). Indoleamine 2,3-dioxygenase degrades tryptophan to formyl-kynurenine in the cytosol. Accordingly, KB cells were seeded at 10%, 25%, 50% dilution (derived from a suspension that was from ~90% confluent plate). Interferon gamma (IFNγ) was added at 500 and 1000 U/ml. KB cells used as a control (i.e. no IFNγ) were seeded at 10% dilution only. KB cells were incubated in growth medium (MEM-alpha, 10° A FBS (fetal bovine serum), penicillin/streptomycin) and then in OPTIMEM for 4 days prior to imaging. Cells were transfected (in OPTIMEM) with the pTK222c construct 1 day prior to imaging. IFNγ was maintained during transfection in OPTIMEM. Three hours prior to imaging, the cells were incubated in growth medium (containing IFNγ in the respective cultures). After three hours, the growth medium was exchanged with Tyrode's solution and the cells were kept in incubation chamber until analysis. The cells were perfused with 1 μM, 5 μM, 50 μM, and 100 μM L-tryptophan in Tyrode's solution.

Figure 11A:
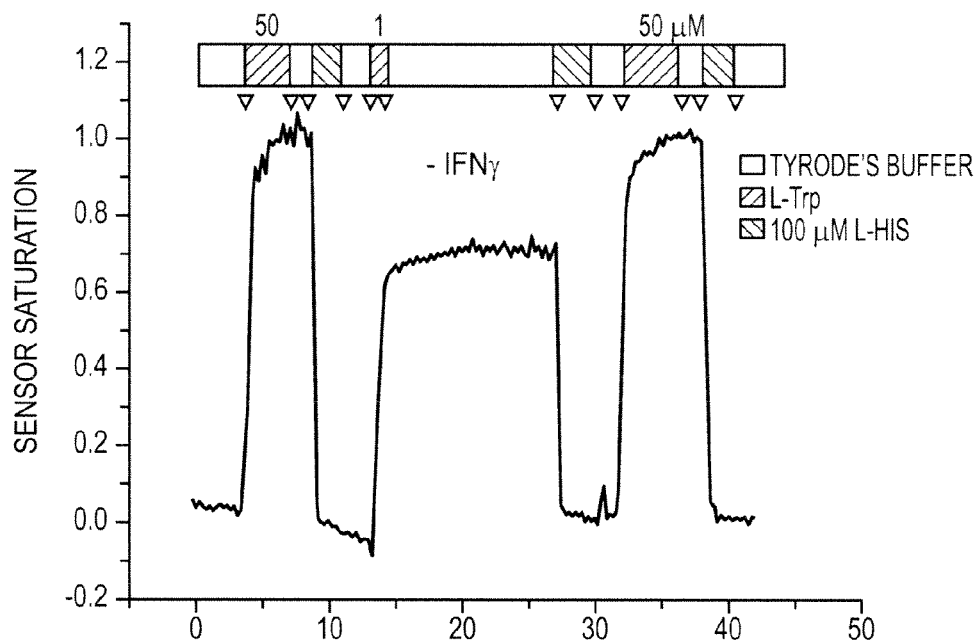
FIGS. 11A-B show the effect of Interferon-γ on Intracellular Tryptophan Concentration.

In FIG. 11A, an untreated KB cell is loaded with tryptophan until the sensor is saturated. Perfusion with histidine brings the response back to baseline levels. Next the cell is loaded until the sensor is partially saturated and small changes in tryptophan concentration can be easily detected. In the untreated cell the tryptophan level stays constant during continuous perfusion with Tyrode's buffer and only perfusion with histidine brings the response back to baseline levels. Final perfusion with tryptophan and histidine is used to redetermine the maximal response of the sensor.

Figure 11B:
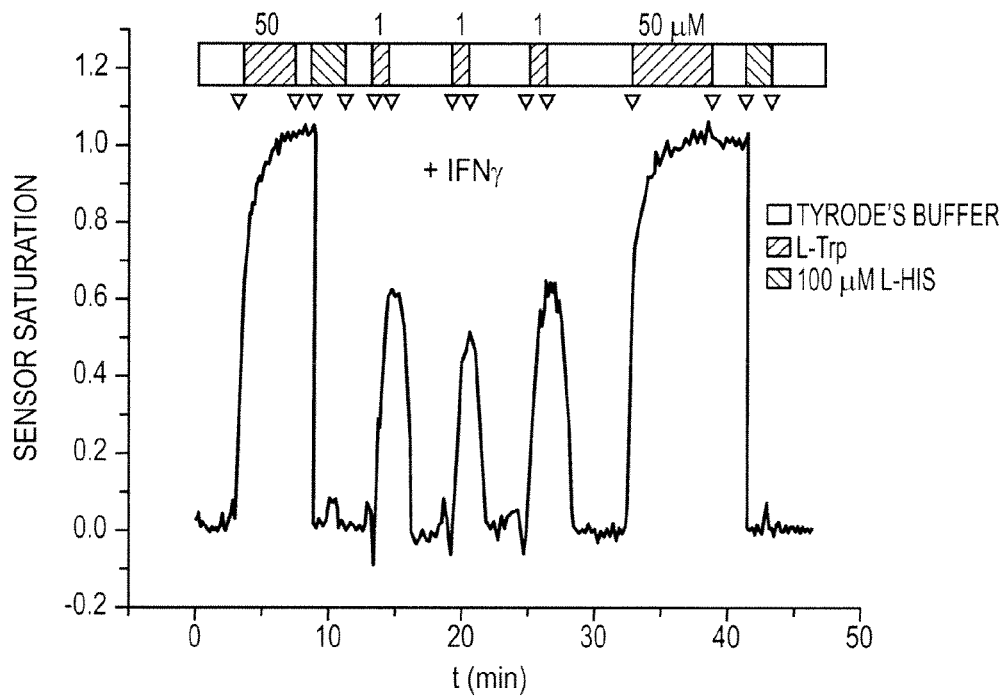

In FIG. 11B, a KB cell treated with 500 U/ml IFNγ is loaded with tryptophan to determine the maximal sensor response and unloaded with histidine. This time when the cell is loaded until the sensor is partially saturated the levels drop immediately when the cells is perfused with Tyrode's buffer. Within minutes the baseline level is reached. This process is repeatable. Final perfusion with tryptophan and histidine shows again the maximal response of the sensor.

Based on these data, IFNγ treatment induces mechanisms in KB cells that lower the intracellular tryptophan concentration. The mechanism for this phenomenon can be readily explained as either: (1) enzymatic degradation by induced IDO; and (2) efflux through a transporter induced by IFNγ. Also, the data confirm that FRET nanosensors can be used to monitor the metabolism of tryptophan.

Discussion

Mammalian cells cannot synthesize the amino acid tryptophan and rely on its transport as tryptophan or as components of nutrients such as peptides across the plasma membrane for basic cell functioning. Tryptophan is necessary for protein synthesis, as it accounts for 1.3% of the amino acids in human proteins. Tryptophan is also the precursor of other vital molecules like serotonin, melatonin and NAD. Moreover, kynurenines produced from tryptophan appear to play a pivotal role in immunosuppression in inflammatory diseases and cancer.

The FLIPW nanosensors described in this study allow for non-invasive real-time, spatio-temporal imaging of intracellular tryptophan levels and flux, offering advantages over conventional analytic methods. The *E. coli* transcriptional regulator TrpR was employed as the recognition element for the construction of FRET sensors for tryptophan. As noted previously, the use of bacterial proteins for the construction of intracellular sensors reduces the problem of cross-interference with endogenous metabolic and signal transduction pathways in eukaryotic cells (Belousov et al., 2006). Genetically-encoded nanosensors further offer the advantage of subcellular sensor targeting through judicious choice of leader sequences as demonstrated by nuclear- and ER-targeted glucose nanosensors (Fehr et al., 2004; Fehr et al., 2005) and cell-surface display of a glutamate nanosensor (Okumoto et al., 2005). Most FRET nanosensors have been based on the ligand-binding-induced Venus-fly-trap-like conformational changes of bacterial periplasmic binding proteins (PBPs) (Fehr et al., 2002; Fehr et al., 2003; Lager et al., 2003; Okumoto et al., 2005), which consist of two well-structured lobes with the ligand-binding site located at the interface. TrpR is about three times smaller than the average PBP and is partially unfolded in the absence of tryptophan (Reedstrom and Royer, 1995). In the presence of tryptophan the protein adopts the conformation observed in crystal structures (Zhang et al., 1987) and the concomitant conformational changes allow for the detection of tryptophan binding by FRET. The FLIPW sensors, therefore, represent a novel class of nanosensors.

FRET has been a successful reporter signal for small molecule sensors (De et al., 2005; Lalonde et al., 2005). According to the Förster theory, the efficiency of the energy transfer depends on the distance between the fluorophores and their dipole orientation (Jares-Erijman and Jovin, 2003). These small molecule nanosensors can be engineered by modification of linker sequences between reporter and sensing domains and/or insertion of fluorophores in surface loops of the sensing domain, resulting in increased and/or reversed signal outputs of FRET nanosensors (Deuschle et al., 2005). Since TrpR dimerizes to form its ligand-binding sites, a novel approach for engineering of the FRET signal was applied. Insertion of a second TrpR coding sequence in the principal FLIPW-CTY sensor changed the FRET response depending on the position of the insertion site. While insertion before eCFP and between eCFP and Venus almost eliminated the FRET response, a TrpR copy after Venus reversed the FRET response and increased the ratio change. Comparison of structural models of the FLIPW-CTY and FLIPW-CTYT sensors predicted that the fluorophores would be closer together in FLIPW-CTY. Since FRET efficiency is inversely correlated with the distance between the fluorophores as described in the Förster equation (Jares-Erijman and Jovin, 2003), the experimentally determined FRET ratio and the models are consistent.

FLIPW-CTYT was used for monitoring tryptophan uptake in cell cultures grown in 96-well microtiter plates, which makes the sensor suitable for high-throughput assays in which the effect of drugs or siRNAs is tested systematically (Myers et al., 2003). The effective $K_M$ for combined tryptophan uptake and metabolism in COS-7 cells in microplate assays and during perfusion was similar with values in the low micromolar range. It was found that LAT1 is responsible for the observed tryptophan exchange in COS-7 cells. The affinity of LAT1 for tryptophan uptake is 21.4 μM (Yanagida et al., 2001) and relates to the sum of intracellular pools of free, incorporated, and degraded tryptophan in oocytes. Affinities obtained using FLIPW-CTYT, on the other hand, are more specific as they have been determined for the pool of free tryptophan in the targeted subcellular compartment.

Transporters LAT1 and LAT2 are heteromeric obligatory counterexchangers of large, neutral amino acids with a 1:1 exchange stoichiometry (Meier et al., 2002; Verrey, 2003). As exchangers, they do not change the overall intracellular amino acid concentration, but rather modify their relative concentrations. Perfusion of FLIPW-CTYT-expressing COS-7 cells with tryptophan and histidine yielded high resolution data of the real-time dynamics of free cytosolic tryptophan resulting from system L countertransport activity. Importantly, it was found that LAT transporters can exchange kynurenines and tryptophan, which has not been demonstrated before. Since the individual intracellular and extracellular substrate selectivities of the LAT transporters are the same (Meier et al., 2002), kynurenine-tryptophan exchange can occur in both directions.

Figure 6:
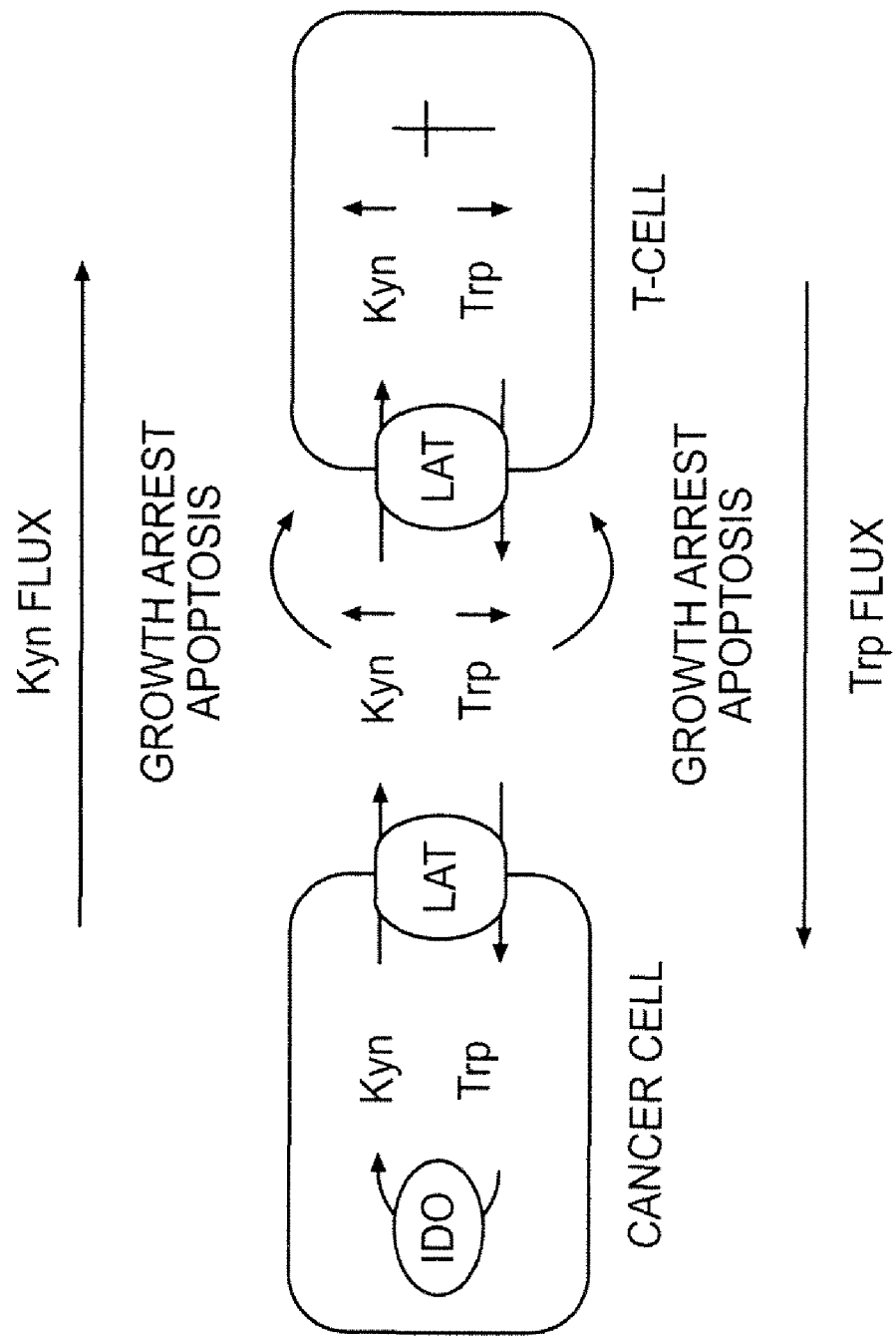
FIG. 6 illustrates the double trouble for T-cells: proposed model for the contribution of LAT-mediated tryptophan-kynurenine exchange to inflammation and immune escape. IDO- and LAT-expressing cell types such as cancer cells replace tryptophan in the local environment with kynurenines. On the one hand, T-cells, expressing LAT transporters (black circle) for the transport of tryptophan (Seymour et al. (2006) J. Leukoc. Biol. 80:1320-1327), are drained of tryptophan; on the other hand, kynurenine levels increase. Both result in T-cell growth arrest and apoptosis (Fallarino et al. (2003) Adv. Exp. Med. Biol. 527; Frumento et al. (2002) J. Exp. Med. 196:459-468; Lee et al. (2002) Immunology 107:452-460).

Tryptophan-kynurenine exchange may represent an endogenous immunosuppressive mechanism during autoimmunity and the immune escape of proliferating cell types like cancer cells by enhancing the depletion of the local tryptophan pool and increasing the kynurenine concentrations (FIG. 6). Kynurenines are produced from tryptophan through IDO, whose enzymatic activity is necessary for immune escape (Muller et al., 2005; Munn et al., 1998). Intracellularly produced kynurenines serve as substrates for the uptake of extracellular tryptophan by LAT transporters. Effectively, tryptophan is sequestered from the local environment and kynurenines accumulate in the serum. The kynurenines contribute to the pool of amino acids that can be taken up in exchange for intracellular tryptophan by surrounding cells expressing LAT transporters, which results overall in a tryptophan flux towards the IDO-producing cells. Since resting human T-cells express only transporters of system L for the transport of L-tryptophan (Seymour et al., 2006), the tryptophan-kynurenine exchange mechanism helps to deplete the intracellular tryptophan as well. Both the accumulation of kynurenines and depletion of tryptophan arrest T-cell growth and induce apoptosis (Fallarino et al., 2003; Frumento et al., 2002; Lee et al., 2002). Thus, tryptophan-kynurenine exchange results in double trouble for T-cells (FIG. 6). At the same time, IDO overproducing cells are protected from the apoptotic effect of kynurenines by the strict counterexchange of tryptophan and its stoichiometric degradation products. FLIPW sensors can now be used to test whether T-cells take up kynurenines using the same pathway leading to a further drain of the essential tryptophan. The sensors can also be used to identify novel drugs and regulatory factors in genomic RNAi screens or screens of chemical libraries.

Figure 9A:
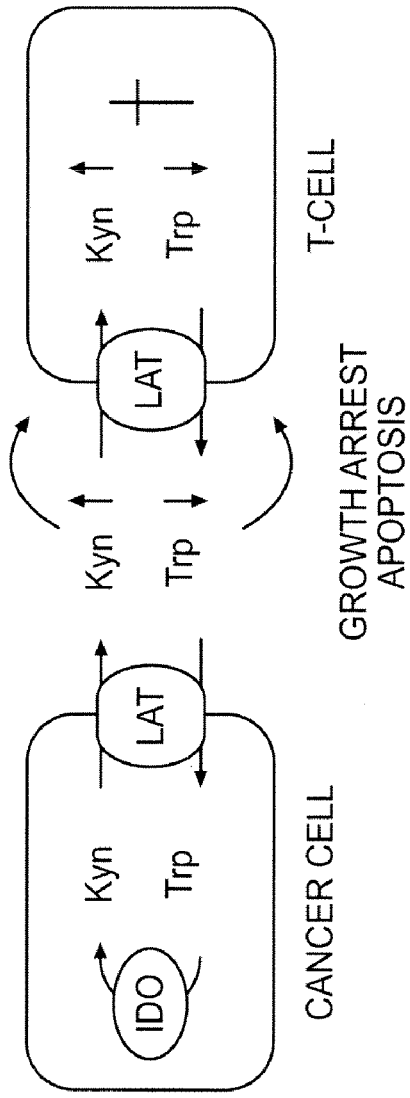
FIGS. 9A-B show the proposed mechanism for T-cell suppression mediated by the coupled counterexchange of tryptophan for kynurenine.
Figure 9B:
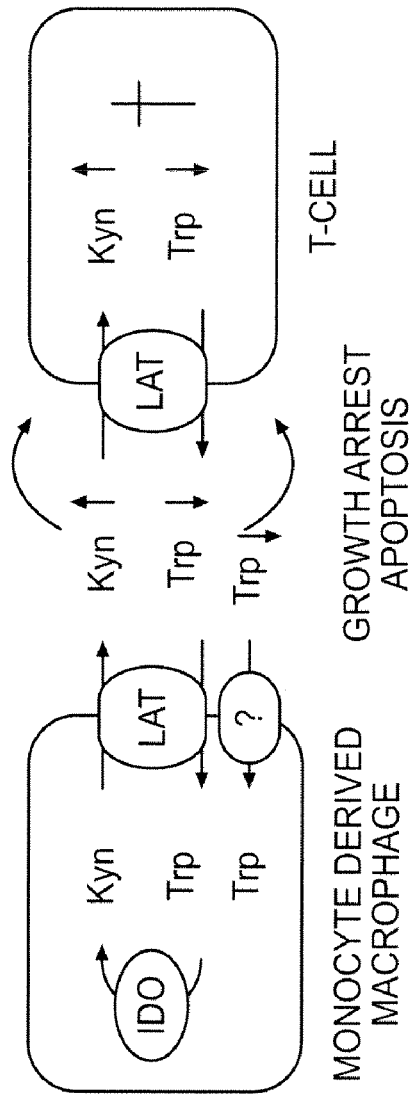
Figure 10:
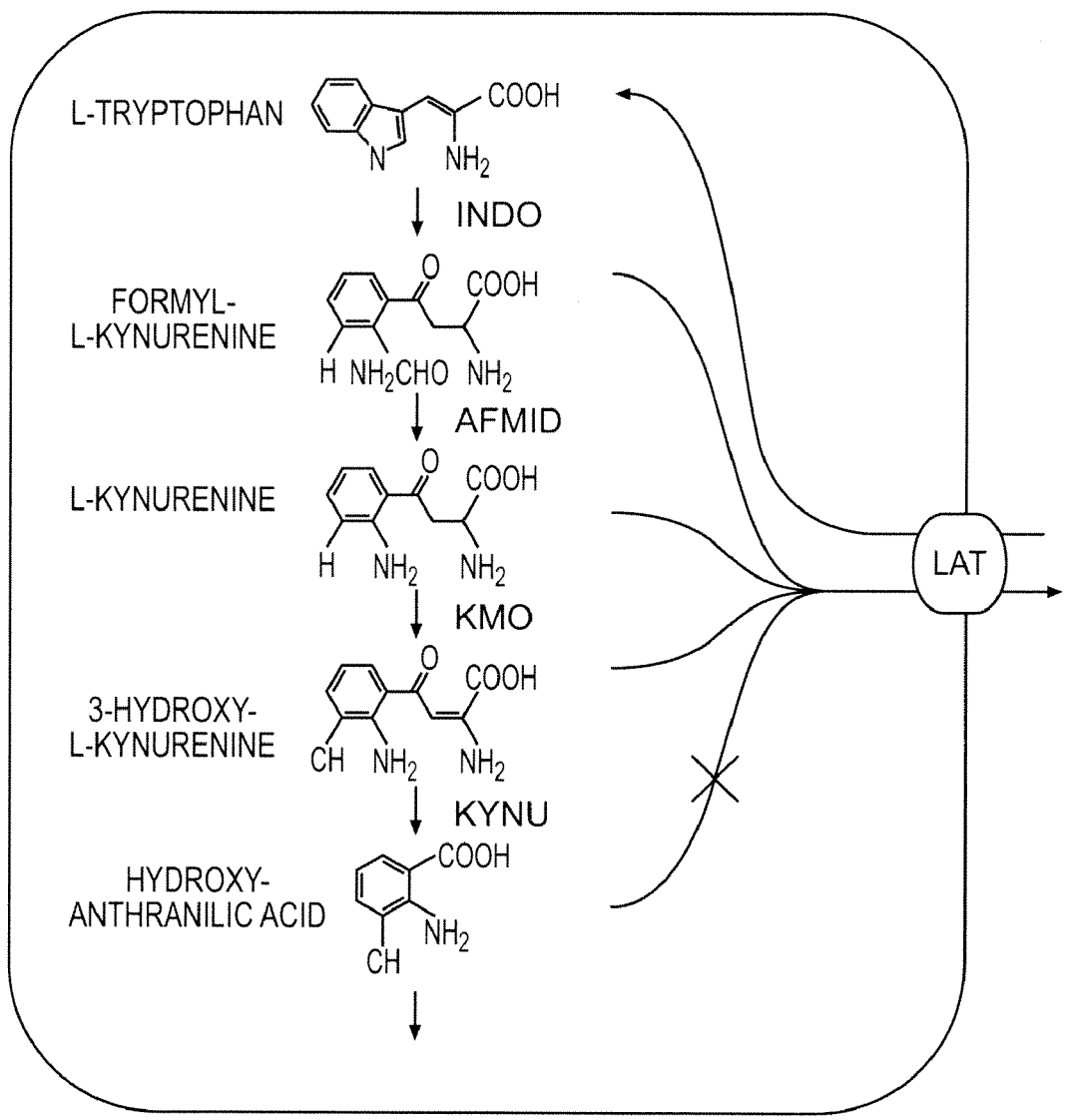
FIG. 10 shows the proposed mechanism for the exchange of tryptophan with its degradation products. The product of tryptophan conversion by IDO is formylkynurenine (FK), which is in turn converted by the enzyme kynurenine formamidase to kynurenine (K). The consecutive action of kynurenine-3-hydroxylase produces 3-hydroxy-kynurenine (HK), which is further degraded by kynureninase to hydroxy-anthranilic acid (HAA). In the proposed mechanism, K and HK are exchanged for tryptophan by the LAT amino acid counterexchanger, while the kynurenine degradation product, HAA, is not exchanged for tryptophan. Black circle represents LAT transporter.

The coupled counterexchange of tryptophan for kynurenine or its degradation products contributes to natural T-cell suppression as exerted by monocyte-derived macrophages (MDMs) and other antigen presenting cells through IDO-conversion of tryptophan to kynurenines. Recently, Seymore and coworkers found that MDMs express next to system L transporters, a second transport system for the efficient depletion of the available tryptophan (Seymour et al., 2006, which is herein incorporated by reference in its entirety). The system is highly selective for tryptophan and has a higher affinity for tryptophan than LAT transporters. It enables MDMs to reduce tryptophan levels below those necessary for LAT-mediated uptake. The kynurenines that MDMs produce can be excreted in exchange for other large neutral amino acids by the available LAT transporters. As a result, T-cell growth is efficiently halted and the cells will be prone to apoptosis (Fallarino et al., 2003; Frumento et al., 2002; Lee et al., 2002, each of which are herein incorporated by reference in its entirety) (FIG. 9A-B).

FRET nanosensors are unique tools for studying intracellular small molecule steady state levels and fluxes in vivo and in real-time. Ultimately, complete metabolic routes can be monitored by employing nanosensors that selectively detect single intermediates. For this means, a set of FRET nanosensors has been constructed that employ the ligand-induced conformational changes of PBPs (Fehr et al., 2002; Fehr et al., 2003; Lager et al., 2003; Okumoto et al., 2005). As the FLIPW sensors demonstrate, other protein scaffolds that undergo conformational changes upon ligand binding can provide sensing domains for nanosensors with specificities not represented in the PBP family, such as tryptophan. E. coli tryptophan repressor TrpR is not part of a protein family with different substrate specificities, which could be used for the expansion of the current set of nanosensors. However, the wealth of bacterial transcriptional regulators, which change affinity for operator sequences upon binding of effectors, may provide potential sensing domains for novel FRET metabolite nanosensors.

The FLIPW-CTYT nanosensor has proven to be a robust system with multiple advantages over conventional methods for intracellular tryptophan detection. The new sensor thus provides a complementary tool for monitoring steady state levels, uptake, and counterexchange, and will be an important tool for analyzing the factors that control tryptophan flux in living cells. As the kynurenine/tryptophan exchange demonstrates such factors might contribute to important cellular processes such as inflammation and immune escape.

All publications, patents and patent applications discussed herein are incorporated herein by reference in their entireties. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

Babu, E., Kanai, Y., Chairoungdua, A., Kim do, K., Iribe, Y., Tangtrongsup, S., Jutabha, P., Li, Y., Ahmed, N., Sakamoto, S., et al. (2003). Identification of a novel system L amino acid transporter structurally distinct from heterodimeric amino acid transporters. The Journal of Biological Chemistry 278(44), 43838-43845.

Belousov, V. V., Fradkov, A. F., Lukyanov, K. A., Staroverov, D. B., Shakhbazov, K. S., Terskikh, A. V., and Lukyanov, S. (2006). Genetically encoded fluorescent indicator for intracellular hydrogen peroxide. Nat Methods 3, 281-286.

Bodoy, S., Martain, L., Zorzano, A., Palacain, M., Estacvez, R., Bertran, J., Department of, B., and Molecular Biology, U. o. B. A. D. B. E. S. (2005). Identification of LAT4, a novel amino acid transporter with system L activity. The Journal of Biological Chemistry 280(12), 12002-12011.

Broer, S., Cavanaugh, J. A., and Rasko, J. E. J. (2005). Neutral amino acid transport in epithelial cells and its malfunction in Hartnup disorder. Biochem Soc Trans 33, 233-236.

De, S., Macara, I. G., and Lannigan, D. A. (2005). Novel biosensors for the detection of estrogen receptor ligands. J Steroid Biochem Mol Biol 96, 235-244.

Deuschle, K., Okumoto, S., Fehr, M., Looger, L. L., Kozhukh, F., and Frommer, W. B. (2005). Construction and optimization of a family of genetically encoded metabolite sensors by semirational protein engineering. Protein Sci 14, 2304-2314.

Fallarino, F., Grohmann, U., Vacca, C., Orabona, C., Spreca, A., Fioretti, M. C., Puccetti, P., and Department of Experimental Medicine, U. o. P. I. ft. i. (2003). T cell apoptosis by kynurenines. Adv Exp Med Biol 527.

Fehr, M., Frommer, W. B., and Lalonde, S. (2002). Visualization of maltose uptake in living yeast cells by fluorescent nanosensors. Proc. Natl. Acad. Sci. U.S.A. 99, 9846-9851.

Fehr, M., Lalonde, S., Ehrhardt, D. W., and Frommer, W. B. (2004). Live imaging of glucose homeostasis in nuclei of COS-7 cells. J Fluoresc 14, 603-609.

Fehr, M., Lalonde, S., Lager, I., Wolff, M. W., and Frommer, W. B. (2003). In vivo imaging of the dynamics of glucose uptake in the cytosol of COS-7 cells by fluorescent nanosensors. J Biol Chem 278, 19127-19133.

Fehr, M., Takanaga, H., Ehrhardt, D. W., and Frommer, W. B. (2005). Evidence for high-capacity bidirectional glucose transport across the endoplasmic reticulum membrane by genetically encoded fluorescence resonance energy transfer nanosensors. Mol Cell Biol 25, 11102-11112.

Feliubadalo, L., Font, M., Purroy, J., Rousaud, F., Estivill, X., Nunes, V., Golomb, E., Centola, M., Aksentijevich, I., Kreiss, Y., et al. (1999). Non-type I cystinuria caused by mutations in SLC7A9, encoding a subunit (bo,+AT) of rBAT. Nat Genet 23, 52-57.

Frumento, G., Rotondo, R., Tonetti, M., Damonte, G., Benatti, U., Ferrara, G. B., and Ibanez, A. NI. (2002). Tryptophan-derived catabolites are responsible for inhibition of T and natural killer cell proliferation induced by indoleamine 2,3-dioxygenase. J Exp Med 196, 459-468.

Gingrich, J. A., and Hen, R. (2001). Dissecting the role of the serotonin system in neuropsychiatric disorders using knockout mice. Psychopharmacology (Berl) 155, 1-10.

Gryk, M. R., Jardetzky, O., Klig, L. S., and Yanofsky, C. (1996). Flexibility of DNA binding domain of trp repressor required for recognition of different operator sequences. Protein Sci 5, 1195-1197.

Gunsalus, R. P., and Yanofsky, C. (1980). Nucleotide sequence and expression of *Escherichia coli* trpR, the structural gene for the trp aporepressor. Proc. Natl. Acad. Sci. U.S.A. 77(12), 7117-7121.

Jares-Erijman, E. A., and Jovin, T. M. (2003). FRET imaging. Nat Biotechnol 21, 1387-1395.

Joachimiak, A., Kelley, R. L., Gunsalus, R. P., Yanofsky, C., and Sigler, P. B. (1983). Purification and characterization of trp aporepressor. Proc Natl Acad Sci USA 80(3), 668-672.

Kanai, Y., Segawa, H., Miyamoto, K., Uchino, H., Takeda, E., and Endou, H. (1998). Expression cloning and characterization of a transporter for large neutral amino acids activated by the heavy chain of 4F2 antigen (CD98). J Biol Chem 273, 23629-23632.

Kim, D. K., Kanai, Y., Matsuo, H., Kim, J. Y., Chairoungdua, A., Kobayashi, Y., Enomoto, A., Cha, S. H., Goya, T., and Endou, H. (2002). The human T-type amino acid transporter-1: characterization, gene organization, and chromosomal location. Genomics 79, 95-103.

Lager, I., Fehr, M., Frommer, W. B., and Lalonde, S. (2003). Development of a fluorescent nanosensor for ribose. FEBS Lett 553, 85-89.

Lakowicz, J. R. (1999). Principles of fluorescence spectroscopy. In (New York, Kluwer Academic), pp. 237-265.

Lalonde, S., Ehrhardt, D. W., and Frommer, W. B. (2005). Shining light on signaling and metabolic networks by genetically encoded biosensors. Curr Opin Plant Biol 8, 574-581.

LaMorte, V. J., Zoumi, A., and Tromberg, B. J. (2003). Spectroscopic approach for monitoring two-photon excited fluorescence resonance energy transfer from homodimers at the subcellular level. J Biomed Opt 8, 357-361.

Lee, G. K., Park, H. J., Macleod, M., Chandler, P., Munn, D. H., and Mellor, A. L. (2002). Tryptophan deprivation sensitizes activated T cells to apoptosis prior to cell division. Immunology 107, 452-460.

Lu, F., Schumacher, M. A., Arvidson, D. N., Haldimann, A., Wanner, B. L., Zalkin, H., and Brennan, R. G. (1998). Structure-based redesign of corepressor specificity of the *Escherichia coli* purine repressor by substitution of residue 190. Biochemistry 37, 971-982.

Marmorstein, R. Q., Joachimiak, A., Sprinzl, M., and Sigler, P. B. (1987). The structural basis for the interaction between L-tryptophan and the *Escherichia coli* trp aporepressor. J Biol Chem 262, 4922-4927.

Marti-Renom, M. A., Stuart, A. C., Fiser, A., Sanchez, R., Melo, F., and Sali, A. (2000). Comparative protein structure modeling of genes and genomes. Ann Rev Bioph Biomol Struct 29, 291-325.

Meier, C., Ristic, Z., Klauser, S., Verrey, F., Institute of, P., and Institute of Biochemistry, U. o. Z. W. C. H. Z. S. (2002). Activation of system L heterodimeric amino acid exchangers by intracellular substrates. The EMBO journal 21(4), 580-589.

Mellor, A. L., Munn, D., Chandler, P., Keskin, D., Johnson, T., Marshall, B., Jhaver, K., and Baban, B. (2003). Tryptophan catabolism and T cell responses. Adv Exp Med Biol 527.

Muller, A. J., DuHadaway, J. B., Donover, P. S., Sutanto-Ward, E., and Prendergast, G. C. (2005). Inhibition of indoleamine 2,3-dioxygenase, an immunoregulatory target of the cancer suppression gene Bin1, potentiates cancer chemotherapy. Nat Med 11, 312-319.

Munn, D. H., Zhou, M., Attwood, J. T., Bondarev, I., Conway, S. J., Marshall, B., Brown, C., Mellor, A. L., Program in Molecular Immunology, I. o. M. M., and Genetics, M. C. o. G. A. G. A. U.S.A. (1998). Prevention of allogeneic fetal rejection by tryptophan catabolism. Science 281(5380), 1191-1193.

Myers, J. W., Jones, J. T., Meyer, T., and Ferrell, J. E., Jr. (2003). Recombinant Dicer efficiently converts large dsRNAs into siRNAs suitable for gene silencing. Nat Biotechnol 21, 324-328.

Ozaki, Y., Edelstein, M. P., and Duch, D. S. (1988). Induction of indoleamine 2,3-dioxygenase: a mechanism of the antitumor activity of interferon gamma. Proc Natl Acad Sci U.S.A. 85, 1242-1246.

Okumoto, S., Looger, L. L., Micheva, K. D., Reimer, R. J., Smith, S. J., and Frommer, W. B. (2005). Detection of glutamate release from neurons by genetically encoded surface-displayed FRET nanosensors. Proc Natl Acad Sci USA 102, 8740-8745.

Otwinowski, Z., Schevitz, R. W., Zhang, R. G., Lawson, C. L., Joachimiak, A., Marmorstein, R. Q., Luisi, B. F., and Sigler, P. B. (1988). Crystal structure of trp repressor/operator complex at atomic resolution. Nature 335, 321-329.

Pfeiffer, R., Rossier, G., Spindler, B., Meier, C., Kuhn, L., and Verrey, F. (1999) Amino acid transport of y+L-type by heterodimers of 4F2hc/CD98 and members of the glycoprotein-associated amino acid transporter family. Embo J 18, 49-57.

Pineda, M., Fernandez, E., Torrents, D., Estevez, R., Lopez, C., Camps, M., Lloberas, J., Zorzano, A., and Palacin, M. (1999). Identification of a membrane protein, LAT-2, that Co-expresses with 4F2 heavy chain, an L-type amino acid transport activity with broad specificity for small and large zwitterionic amino acids. J Biol Chem 274, 19738-19744.

Platten, M., Ho, P. P., Youssef, S., Fontoura, P., Garren, H., Hur, E. M., Gupta, R., Lee, L. Y., Kidd, B. A., Robinson, W. H., et al. (2005). Treatment of autoimmune neuroinflammation with a synthetic tryptophan metabolite. Science 310, 850-855.

Reedstrom, R. J., and Royer, C. A. (1995). Evidence for coupling of folding and function in trp repressor: physical characterization of the superrepressor mutant AV77. J Mol Biol 253, 266-276.

Rossier, G., Meier, C., Bauch, C., Summa, V., Sordat, B., Verrey, F., and Kuhn, L. C. (1999). LAT2, a new basolateral 4F2hc/CD98-associated amino acid transporter of kidney and intestine. J Biol Chem 274, 34948-34954.

Saper, C. B., Scammell, T. E., and Lu, J. (2005). Hypothalamic regulation of sleep and circadian rhythms. Nature 437, 1257-1263.

Schevitz, R. W., Otwinowski, Z., Joachimiak, A., Lawson, C. L., and Sigler, P. B. (1985). The three-dimensional structure of trp repressor. Nature 317, 782-786.

Seymour, R. L., Ganaphthy, V., Mellor, A. L., and Munn, D. H. (2006). A high-affinity, tryptophan-selective amino acid transport system in human macrophages. J Leukoc Biol 80, 1320-1327.

Torrents, D., Estevez, R., Pineda, M., Fernandez, E., Lloberas, J., Shi, Y. B., Zorzano, A., and Palacin, M. (1998). Identification and characterization of a membrane protein (y+L amino acid transporter-1) that associates with 4F2hc to encode the amino acid transport activity y+L. A candidate gene for lysinuric protein intolerance. J Biol Chem 273, 32437-32445.

Van der Meer, B. W., Cooker, G. I., and Chen, S. Y. S. (1994). Resonance energy transfer (New York, VCH Publishers).

Verrey, F. (2003). System L: heteromeric exchangers of large, neutral amino acids involved in directional transport. Eur J Physiol 44, 529-533.

Yanagida, O., Kanai, Y., Chairoungdua, A., Kim, D. K., Segawa, H., Nii, T., Cha, S. H., Matsuo, H., Fukushima, J., Fukasawa, Y., et al. (2001). Human L-type amino acid transporter 1 (LAT1): characterization of function and expression in tumor cell lines. Biochim Biophys Acta 1514, 291-302.

Yanofsky, C. (1981). Attenuation in the control of expression of bacterial operons. Nature 289, 751-758.

Zhang, R. G., Joachimiak, A., Lawson, C. L., Schevitz, R. W., Otwinowski, Z., and Sigler, P. B. (1987). The crystal structure of trp aporepressor at 1.8 A shows how binding tryptophan enhances DNA affinity. Nature 327, 591-597.

---

What is claimed:

1. An isolated nucleic acid encoding a tryptophan nanosensor fusion protein comprising a donor fluorophore moiety, an acceptor moiety, a first tryptophan binding moiety and a second tryptophan binding moiety, wherein the first tryptophan binding moiety dimerizes with the second tryptophan binding moiety in the presence of tryptophan thereby causing a change in Förster Resonance Energy Transfer (FRET) between the donor moiety and the acceptor moiety.

2. The isolated nucleic acid of claim 1, wherein the donor moiety is between the first tryptophan binding moiety and the second tryptophan binding moiety.

3. The isolated nucleic acid of claim 1, wherein the acceptor moiety is between the first tryptophan binding moiety and the second tryptophan binding moiety.

4. The isolated nucleic acid of claim 1, wherein the donor moiety and the acceptor moiety flank the first tryptophan binding moiety and the second tryptophan binding moiety.

5. The isolated nucleic acid of claim 1, further comprising a linker moiety.

6. The isolated nucleic acid of claim 1, wherein the donor and acceptor moieties are be selected from the group consisting of GFP (green fluorescent protein), CFP (cyan fluorescent protein), BFP (blue fluorescent protein), OFP (orange fluorescent protein), RFP (red fluorescent protein), YFP (yellow fluorescent protein), enhanced CFP (eCFP), enhanced YFP (EYFP), DsRed, DsRed2, MiCy, mKO, and Venus EFP.

7. The isolated nucleic acid of claim 1, wherein the donor moiety is eCFP.

8. The isolated nucleic acid of claim 1, wherein the acceptor moiety is Venus YFP.

9. The isolated nucleic acid of claim 1, further comprising a targeting sequence.

10. An expression vector comprising the isolated nucleic acid of claim 1.

11. A cell comprising the isolated nucleic acid of claim 1.

12. The isolated nucleic acid of claim 1, wherein the tryptophan binding moiety is TrpR.

13. The isolated nucleic acid of claim 1, wherein the tryptophan binding moiety comprises the amino acid sequence as set forth in SEQ ID NO: 1.

14. The isolated nucleic acid of claim 1, wherein the tryptophan binding moiety consists of the amino acid sequence as set forth in SEQ ID NO: 1.

\* \* \* \* \*